(12) United States Patent
Yong et al.

(10) Patent No.: US 7,033,582 B2
(45) Date of Patent: Apr. 25, 2006

(54) USE OF GLATIRAMER ACETATE (COPOLYMER 1) IN THE TREATMENT OF CENTRAL NERVOUS SYSTEM DISORDERS

(75) Inventors: V. Wee Yong, Calgary (CA); Sophie Chabot, Montreal (CA)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

(21) Appl. No.: 10/920,136

(22) Filed: Aug. 17, 2004

(65) Prior Publication Data

US 2005/0014694 A1 Jan. 20, 2005

Related U.S. Application Data

(63) Continuation of application No. 09/875,429, filed on Jun. 5, 2001, now abandoned.

(60) Provisional application No. 60/209,372, filed on Jun. 5, 2000.

(51) Int. Cl.
| | |
|---|---|
| *A61K 38/00* | (2006.01) |
| *A61K 9/00* | (2006.01) |
| *A61K 9/10* | (2006.01) |
| *A61K 9/20* | (2006.01) |
| *A61K 9/48* | (2006.01) |

(52) U.S. Cl. .................. 424/78.08; 424/400; 424/439; 424/451; 424/464

(58) Field of Classification Search ................ 424/400, 424/449, 448, 434, 422, 78.08, 439, 451, 424/464
See application file for complete search history.

(56) References Cited

U.S. PATENT DOCUMENTS

| | | | |
|---|---|---|---|
| 3,849,550 | A | 11/1974 | Teitelbaum et al. |
| 3,991,210 | A | 11/1976 | Shea |
| 4,129,666 | A | 12/1978 | Wizerkaniuk |
| 4,339,431 | A | 7/1982 | Gaffar |
| 5,204,099 | A | 4/1993 | Barbier et al. |
| 5,554,372 | A | 9/1996 | Hunter |

(Continued)

FOREIGN PATENT DOCUMENTS

EP 0383620 A2 8/1990

(Continued)

OTHER PUBLICATIONS

Teitelbaum et al., "Suppression of Experimental Allergic Encephalomyelitis by a Synthetic Polypeptide", *Israel J. Med. Sci.*, 1971, 7, 630-631 (Abstract).

(Continued)

*Primary Examiner*—Thurman K. Page
*Assistant Examiner*—Simon Oh
(74) *Attorney, Agent, or Firm*—John P. White, Esq.; Cooper & Dunham LLP

(57) ABSTRACT

The present invention involves the administration of Copolymer 1 (glatiramer acetate) to treat inflammatory, non-autoimmune central nervous system (CNS) diseases, alleviate the symptoms thereof, inhibit the activity of matrix metalloproteinases and suppress cytokine production by T lymphocytes.

18 Claims, 11 Drawing Sheets

U.S. PATENT DOCUMENTS

| | | | |
|---|---|---|---|
| 5,583,031 | A | 12/1996 | Stern |
| 5,591,629 | A | 1/1997 | Rodriguez et al. |
| 5,623,052 | A | 4/1997 | McLean et al. |
| 5,627,206 | A * | 5/1997 | Hupe et al. ............... 514/468 |
| 5,688,117 | A | 11/1997 | May et al. |
| 5,719,296 | A | 2/1998 | Acton, III et al. |
| 5,734,023 | A | 3/1998 | Nag et al. |
| 5,800,808 | A | 9/1998 | Konfino et al. |
| 5,858,964 | A | 1/1999 | Aharoni et al. |
| 5,886,156 | A | 3/1999 | McLean et al. |
| 5,958,927 | A | 9/1999 | Peglion et al. |
| 5,965,600 | A | 10/1999 | Sato et al. |
| 5,981,589 | A | 11/1999 | Konfino et al. |
| 6,024,981 | A | 2/2000 | Khankari et al. |
| 6,048,898 | A | 4/2000 | Konfino et al. |
| 6,054,430 | A | 4/2000 | Konfino et al. |
| 6,162,800 | A | 12/2000 | Dolle et al. |
| 6,214,791 | B1 | 4/2001 | Arnon et al. |
| 6,342,476 | B1 | 1/2002 | Konfino et al. |
| 6,362,161 | B1 | 3/2002 | Konfino et al. |
| 6,514,938 | B1 | 2/2003 | Gad et al. |
| 6,620,847 | B1 | 9/2003 | Konfino et al. |
| 6,800,285 | B1 | 10/2004 | Rodriguez et al. |
| 6,800,287 | B1 | 10/2004 | Gad et al. |
| 6,844,314 | B1 | 1/2005 | Eisenbach-Schwartz et al. |
| 2001/0055568 | A1 | 12/2001 | Gilbert et al. |
| 2002/0037848 | A1 | 3/2002 | Eisenbach-Schwartz et al. |
| 2002/0055466 | A1 | 5/2002 | Aharoni et al. |
| 2002/0077278 | A1 | 6/2002 | Yong et al. |
| 2002/0107388 | A1 | 8/2002 | Vanderbark et al. |
| 2003/0004099 | A1 * | 1/2003 | Eisenbach-Schwartz et al. ............ 514/12 |
| 2003/0170729 | A1 | 9/2003 | Klinger |
| 2004/0006022 | A1 | 1/2004 | Strominger et al. |
| 2004/0106554 | A1 | 6/2004 | Konfino et al. |
| 2005/0019322 | A1 | 1/2005 | Rodriguez et al. |
| 2005/0038233 | A1 | 2/2005 | Gad et al. |

FOREIGN PATENT DOCUMENTS

| | | |
|---|---|---|
| EP | 0359783 B1 | 11/1995 |
| WO | WO 9202543 | 2/1992 |
| WO | WO 9403484 | 2/1994 |
| WO | WO 9426774 | 11/1994 |
| WO | WO9526980 | 10/1995 |
| WO | WO 9531990 | 11/1995 |
| WO | WO9531997 | 11/1995 |
| WO | WO 9533475 | 12/1995 |
| WO | WO 9830227 | 7/1998 |
| WO | WO 8810120 | 12/1998 |
| WO | WO0005249 | 2/2000 |
| WO | WO 0005249 | 2/2000 |
| WO | WO 0005250 | 2/2000 |
| WO | WO 0018794 | 4/2000 |
| WO | WO 0020010 | 4/2000 |
| WO | WO 0027417 | 5/2000 |
| WO | WO0152878 | 7/2001 |
| WO | WO0160392 | 8/2001 |
| WO | WO0185797 | 11/2001 |
| WO | WO0193828 | 12/2001 |
| WO | WO0193893 | 12/2001 |
| WO | WO 0197846 | 12/2001 |
| WO | WO02076503 | 10/2002 |
| WO | WO03048935 | 6/2003 |

OTHER PUBLICATIONS

Teitelbaum, et al., "Suppression of Experimental Allergic Encephalomyelitis by a Synthetic Polypeptid", *Eur. J. Immonol.*, 1971, 1, 242-248.

Arnon, et al., "Suppression of Experimental Allergic Encephalomyelitis by a Synthetic Copolymer Immunological Cross Reactive with Basic Encephalitogen", *Israel J. Med. Sci.,* 1972, 8, 1759-1760.

Teitelbaum et al., "Protection Against Experimental Allergic Encephalomyelitis", *Nature,* 1972, 240, 564-566.

Webb et al., "Further Studies on the Suppression of Experimental Allergic Encephalomyelitis by Snythetic Copolymer", *Israel J. Med. Sci.,* 1972, 8, 656-657.

Teitelbaum et al., "Suppression Experimental Allergic Encephalomyelitis with Basic Polymers", *Eur. J. Immunol.,* 1973, 3, 273-279.

Webb, et al., "In Vivo and in Vitro Immunological Cross-reactions between Basic Encephalitogen and Synthetic Basic Polypeptides Capable of Suppressing Experimental Allergic Encephalomyelitis", Eur. J. Immunol., 1973, 3, 279-286.

Teitelbaum et al., "Dose-response Studies on Experimental Allergic Encephalomyelitis Suppression by COP-I", *Israel J. Med. Sci.,* 1974, 10(9), 1172-1173.

Teitelbaum, et al., "Suppression of Experimental Allergic Encephalomyelitis in Rhesus Monkeys by a Synthetic Basic Copolymer", *Clin. Immunol. Immunopath.,* 1974, 3, 256-262.

Webb et al., "Suppression of Experimental Allergic Encephalomyelitis in Rhesus Monkeys by a Synthetic Basic Copolymer", *Israel J. Med. Sci.,* 1975, 11, 1388 (Abstract).

Webb, et al., "Molecular Requirements Involved in Suppression of EAE by Synthetic Basic Copolymers of Amino Acids", *Immunochem.,* 1976, 13, 333-337.

Abramsky, et al., "Effect of a Synthetic Polypeptide (COP-1) on Patients with Multiple Sclerosis and with Acute Disseminated Encephalomyelitis", *J. Neurol. Sci.,* 1977, 31, 433-438.

Teitelbaum, et al., "suppression Experimental Allergic Encephalomyelitis in Baboons by Cop 1", *Israel J. Med. Sci.,* 1977, 13, 1038 (Abstract).

Arnon, et al., "Suppression of EAE in Baboons by a Synthetic Polymer of Amino Acids", *Neurol.,* 1978, 28, 336 (Abstract).

Sela, et al., "Experimental Allergic Encephalomyelitis" in *Menarini Series on Immunopathology,* vol. 1, First Symposium of Organ Specific Autoimmunity, Cremona, Italy, Jun., 1977, (Miescher P.A. ed., Schwabe Co., Basel, 1978), 9-21.

Alvord, et al., "Myelin Basic Protein Treatment of Experimental Allergic Encephalomyelitis in Monkeys", *Ann. Neurol.,* 1979, 6, 469-473.

Keith, et al., "The Effect of COP 1, a Synthetic Polypeptide, on Chronic Relapsing Experimental Allergic Encephalomyelitis in Guinea Pigs" *J. Neurol. Sci.,* 1979, 42, 267-274.

Lando, et al., "Effect of Cyclophosphamide on Suppressor Cell Activity in Mice Unresponsive to EAE", *J. Immunol.,* 1979, 123, 2156-2160. (Abstract).

Lando, et al., "Experimental Allergic Encephalomyelitis in Mice—Suppresion and Prevention with COP-1", *Israel J. Med. Sci.,* 1979, 15, 868-869 (Abstract).

Teitelbaum, et al., "Blocking of Sensitization to Encephalitogenic Basic Protein in Vitro by Synthetic Basic Copolymer (COP 1)" in *Cell Biology and Immunology of Leukocyte Function* (Academic Press, New York, 1979) 681-685.

Teitelbaum, "Suppression of Experimental Allergic Encephalomylitis with a Synthetic Copolymer—Relevance to Multiple Sclerosis", in *Humoral Immunity in Neurological Diseases* (Karcher D., Lowenthal A. & Strosberg A.D., eds., Plenum Publishing Corp., 1979) 609-613.

Arnon, et al., "Desensitization of Experimental Allergic Encephalomyelitits with Synthetic Peptide Analogues" in *The Suppression of Experimental Allergic Encephalomyelitis and Multiple Sclerosis* (Academic Prss, New York, 1980) 105-107.

Arnon, "A Synthetic Copolymer of Amino Acids in a Clinical Trial for MS Therapy" in *Progress in Multiple Sclerosis Research* (Bauer, Ritter, eds., Springer Verlag New York, 1980) 416-418.

Bornstein, et al., "Treatment of Multiple Sclerosis with a Synthetic Polypeptide: Preliminary Results", *ann. Neurol.*, 1980, 8, 117 (Abstract).

Bornstein, et al., "Treatment of Multiple Sclerosis with a Synthetic Polypeptide: Preliminary Results", *Trans. Am. Neurol. Assoc.*, 1980 105, 348-350.

McDermott, et al., "Antigen-induced Suppression of Experimental Allergic Neuritis in the Guinea Pig", *J. Neurol. Sci.*, 1980, 46, 137-143.

Arnon, "Experimental Allergic Encephalomyelitis—Susceptibility and Suppression", *Immunological Rev.*, 1981, 55, 5-30.

Bornstein, et al., "Multiple Sclerosis: Trial of a Synthetic Polypeptide", *Ann. Neurol.*, 1982, 11, 317-319.

Brosnan, et al., "The Response of Normal Lymphocytes to Copolymer 1", *J. Neuropath. Exp. Neurol.*, 1983, 42, 356 (Abstract).

Lisak, et al., "Effect of Treatment with Copolymer 1 (Cop-1) on the in Vivo and in Vitro Manifestations of Experimental Allergic Encephalomyelitis (EAE)", *J. Neurol. Sci.*, 1983, 62, 281-293.

Bornstein, et al., "Clinical Trials of Copolymer 1 in Multiple Sclerosis"*Ann. N.Y. Acad. Sci. (USA)*, 1984, 366-372.

Bornstein, et al., "Clinical Trials of a Synthetic Polypeptide (Copolymer 1) for the Treatment of Multiple Sclerosis" in Gonsett et al., *Immunological and Clinical Aspects of Multiple Sclerosis* (MTP Press, The Hague, 1984) 144-150.

Brosnan, et al., "Copolymer 1: Effect on Normal Human Lymphocytes", *Ann. N.Y. Acad. Sci. (USA)*, 1984, 436, 498-499.

Bornstein, et al., "Multiple Sclerosis: Clinical Trials of a Synthetic Polypeptide, Copolymer 1", *Neurol.*, 1985, 35 (Suppl. 1), 103 (Abstract).

Brosnan, et al., "Immunogenic Potentials of Copolymer 1 in Normal Human Lymphocytes", *Neurol.*, 1985, 35, 1754-1759.

Burns, et al., "Human Cellular Immune Response in Vitro to Copolymer 1 and Myelin Basic Protein (MBP)", *Neurol.*, 1985, 35 (Suppl. 1), 170 (Abstract).

Teitelbaum, et al., "Monoclonal Antibodies to Myelin Basic Protein Cross React with Synthetic EAE-suppressive Copolymer, COP 1" in *Proc. 7th Eur. Immunol. Mtg.*, Jerusalem, Sep. 8-13, 1985 (Abstract).

Thompson, "MCQ Tutor: Medical Immunology Multiple Choice Questions", *Immunol. Today*, 1985, 6(4), 141.

Burns, et al., "Human Cellular Immune Response to Copolymer 1 and Myelin Basic Protein", *Neurol.*, 1986, 36, 92-94.

Bornstein, "Cop 1 May be Beneficial for Patients with Exacerbating-remitting Form of Multiple Scleroisis", *Adv. Ther. (USA)*, 1987, 4, 206 (Abstract).

Bornstein, et al., "A Pilot Trial of Cop 1 in Exacerbating-remitting Multiple Sclerosis", *New Eng. J. Med.*, 1987, 317(7), 408-414.

Rolak, "Copolymer-1 Therapy for Multiple Sclerosis", *Clin. Neuropharmacology*, 1987, 10(5), 389-396.

Winer, "COP 1 Therapy for Multiple Sclerosis", *New Eng. J. Med.*, 1987, 317(7), 442-444.

Arnon, et al., "Suppression of Demyelinating Diseases by Synthetic Copolymers", in *A Multidisciplinary Approach to Myelin Disease* (G. Serlupi Crescenzi, ed., Plenum Publishing Corp., 1988) 243-250.

Baumhefner, et al., "Copolymer 1 as Therapy for Multiple Sclerosis: The Cons", *Neurol.*, 1988, 38(Suppl. 2), 69-71.

Bornstein, et al., "Clinical Experience with COP-1 in Multiple Sclerosis", *Neurol.*, 1988,38(Suppl. 2), 66-69.

Arnon, et al., "Suppression of Experimental Allergic Encephalomyelitis by Cop-1—Relevance to Multiple Sclerosis", *Israel J. Med. Sci.*, 1989, 25, 686-689.

Bornstein, et al., "Pilot Trial of COP-1 in Chronic Progressive Multiple Sclerosis: Preliminary Report", from *The International Multiple Sclerosis Conference: An Update on Multiple Sclerosis*, Roma (Italy), Sep. 15-17, 1988, in *Elsevier Science Publisher*, 1989, 225-232.

Teitelbaum, et al., "Clinical Trial of Copolymer 1 in Multiple Sclerosis" *J. Israel Med. Assoc.*, 1989, CXVI(9), 453-456.

Bornstein, et al., "Clinical Trials of Cop 1 in Multiple Sclerosis" in *Handbook of Multiple Sclerosis* (S.D. Cook Marcel Rekker, ed., 1990) 469-480.

Carter, et al., "Newer Drug Therapies for Multiple Sclerosis", *Drug Therapy*,1990, 31-32, 37-39, 42-43.

Grgacic, et al., "Cell-mediated Immune Response to Copolymer 1 in Multiple Sclerosis Measured by the Macrophage Procoagulant Activity Assay", *Int. Immunol.*, 1990, 2(8), 713-718.

Kay, et al., "The Mechanism of Action of FK 506", *Transplantation Proceedings*, 1990, 22(1, Suppl. 1), 96-99.

Lee, et al., "Peptide and Protein Drug Delivery" in *Advances in Parenteral Sciences*(Vincent H.L. Lee, ed., Marcel Dekker, Inc., 1990) 691-695.

Myers, et al., "The Peculiar Difficulties of Therapeutic Trials for Multiple Sclerosis", *Neurologic Clinics*, 1990, 8(1), 119-141.

Sela, et al., "Suppressive Activity of COP-1 in EAE and its Relevance to Multiple Sclerosis", *Bull. Inst. Pasteur*, 1990, 88, 303-314.

Starzl, *Transplantation Proceedings*, 1990, 22 (1, Suppl. 1), 5.

Wender, "Copolymer 1 (COP-1) in the Treatment of Multiple Sclerosis (letter)" *Neur. Neurochir. Pol.*, 1990, 24, 113.

Bornstein, et al., "A Placebo-controlled, Double-blind, Randomized Two-center, Pilot Trial of Cop 1 in Chronic Progressive Multiple Sclerosis", *Neurol.*, 1991, 41, 533-539.

Burns, et al., "Failure of Copolymer 1 to Inhabit the Human T-cell Response to Myelin Basic Protein", *Neurol.*, 1991, 41, 1317-1319,.

Clinical Trial Protocol No. 9001, Teva Pharmaceutical Industries, Ltd., first patient enrolled Oct. 23, 1991.

Ferrara, et al., "Graft-Versus-Host Disease", *New Eng. J. Med.*, 1991, 324, 667-674.

Meiner, "COP-1 Multicenter Clinical Trial in Exacerbating-remitting Multiple-Sclerosis: One Year Follow-up", *J. Neurol.*, 1991 (Suppl. 1) (Abstract).

Rothbard, et al., "Interactions Between Immunogenic Peptides and MHC Proteins", *Ann. Rev. Immunol.,* 1991, 9, 527-565.

Salvetti, et al., "Myelin Basic Protein T Cell Epitopes in Patients with Multiple Sclerosis", *Department of Neurological Sciences, University of Rome, La Sapienza* 1991, 72 (Abstract).

Teitelbaum, et al., "Cross-reactions and Specificities of Monoclonal Antibodies Against Myelin Basic Protein and Against the Synthetic Copolymer 1", *Proc. Natl. Acad. Sci. (USA),* 1991, 88, 9528-9532.

Van de Bogaerde, et al., "Induction of Long-Term Survival of Hamster Heart Xenografts in Rats", *Transplantation,* 1991, 52, 15-20.

Bornstein, et al., "Treatment of Multiple Sclerosis with Copolymer 1" in *Treatment of Multiple Scleoris: Trial Design, Results and Future Perspectives* (Rudick R.A. & Goodkin D.E., eds., Springer Verlag, London, 1992) 173-198.

Johnson, "Clinical Studies in Copolymer 1 Therapy for Exacerbating-remitting Multiple Sclerosis", in *Congress for Advances in the Understanding and Treatment of Multiple Sclerosis,* Boston (USA), Oct. 28-29, 1992.

Milo, et al., "Inhibition of Myelin Basic Protein-specific Human T-cell Lines by COP-1", *Israel J. Med. Sci.,* 1992, 28, 486 (Abstract).

Racke, et al., "Copolymer-1-induced Inhibition of Antigen-specific T Cell Activation: Interference with Antigen Presentation", *J. Neuroimmunol.,* 1992, 37 75-84.

Teitelbaum, et al., "Synthetic Copolymer 1 Inhibits Human T-cell Lines Specific for Myelin Basic Protein", *Proc. Natl. Acad. Sci. (USA),* 1992, 89, 137-141.

Weinshenker, et al., "Natural History and Treatment of Multiple Sclerosis", *Current Opinion in Neurol. and Neurosurgery,* 1992, 5, 203-211.

Aharoni, et al., "T Suppressor Hybridomas and Interleukin-2-Dependent Lines Induced by Copolymer 1 or by Spinal Cord Homogenate Down-Regulate Experimaental Allergic Encephalomyelitis", *Eur. J. Immunol.,* 1993, 23, 17-25.

Arnon, et al., "Immunomodulation of Experimental Allergic Encephalomyelitis", *Israel J. Med. Sci.,* 1993, 29, 175-181.

Arnon, et al., "On the Existence of Suppressor Cells", *Int. Arch. Allergy Immunol.,* 1993, 100, 2-7.

Clinical Trial Protocol No. 9002, Lemmon Co. and Teva Pharmaceutical Industries, Ltd., first patient enrolled Jun. 17, 1993.

Francis, "The Current Therapy of Multiple Sclerosis", *J. Clin. Pharmacy and Therapeutics,* 1993, 18, 77-84.

Keleman, et al., "Graft-versus-Host Disease in Bone Marrow Transplantation: Experimental, Laboratory, and Clinical Contributions of the Last Few Years", *Int. Arch. Allergy Immunol.,* 1993, 102, 309-320.

Gurevich, "Study of the MHC-competition Between BP and Cop 1 Using Human Cytotoxic T-cell Clones", *Israel J. Med. Sci.,* 1993 (Abstract).

Meiner, et al., "The Israeli COP-1 Multicenter Clinical Trial in Exacerbating-remitting Multiple Sclerosis—Two-year Follow-up", in *9th Congress of the European Committee for Treatment and Research in Multiple Sclerosis,* Florence (Italy), Oct.-Nov., 1993, 48 (Abstract).

Milo, et al., "Copolymer-1 (COP-1) Regulates Class II MHC Expression and Cytokine Synthesis in the THP-1 Monocyte-Macrophage Cell Line" in *The IBC Conference on Multiple Sclerosis,* San Diego (USA), Dec. 10, 1993 (Abstract).

U.S. Appl. No. 09/359,099, filed Jul. 12, 1999, Strominger et al.

Sela, "Polymeric Drugs as Immunomodulatory Vaccines Against Multiple Sclerosis", *Makromol. Chem. Macromol. Symp.,* 1993, 70/71, 147-155.

Arnon, et al., "Immunospecific Drug Design—Prospects for Treatment of Autoimmune Disease", *Therapeutic Immunol.,* 1994, 1, 65-70.

Bansil, et al., "Multiple Sclerosis: Pathogenesis and Treatment", *Seminars in Neurol.,* Jun. 1994, 14(2), 146-153.

The COP-1 Multicenter Clinical and Research Group Study, "COP-1 Multicenter Trial in Relapsing Remitting Multiple Sclerosis: 3 Year Follow Up", *Abstracts of Symposia and Free Communication,* Barcelona (Spain), Jun. 25-29, 1994, 241 (Suppl. 1), 6.

Cotton, "Options for Multiple Sclerosis Therapy", *J.A.M.A Medical News & Perspectives,* 1994, 272(18), 1393.

Dorling, et al., "Prospects for Xenografting", *Curr. Opinions Immunol.,* 1994, 6, 765-769.

Fridkis-Hareli, et al., "Copolymer 1 Displaces MBP, PLP and MOG, but Can Not be Displaced by these Antigens from the MHC Class II Binding Site", *Department of Chemical Immunology, The Weizmann Institute of Science,* 1994.

Fridkis-Hareli, et al., "Direct Binding of Myelin Basic Protein and Synthetic Copolymer 1 to Class II Major Histocompatibility Complex Molecules on Living Antigen-Presenting Cells—Specificity and Promiscuity", *Proc. Natl. Acad. Sci. USA,* 1994, 91, 4872-4876.

Fridkis-Hareli, et al., "Specific and Promiscuous Binding of Synthetic Copolymer 1 to Class II Major Histocompatibility Complex Molecules on Living Antigen Presenting Cells", *Israeli Biochem. Soc.,* 1994, 21-22 (Abstract).

Fridkis-Hareli, et al., "Synthetic Copolymer 1 Inhibits the Binding of MBP, PLP and MOG Peptides to Class II Major Histocompatibility Complex Molecules on Antigen Presenting Cells" in *Neurochem Mtg.,* Aug. 14-19, 1994.

Fridkis-Hareli, et al., "Synthetic Copolymer 1 Inhibits the Binding of MBP, PLP and MOG Peptides to Class II Major Histocompatibility Complex Molecules on Antigen-Presenting Cells", *J. Neurochem.,* 1994, 63(Suppl. I), 561.

Fridkis-Hareli, et al., "Synthetic Copolymer 1 and Myelin Basic Protein Do Not Undergo Processing Prior to the Binding to Class II Major Histocompatibility Complex Molecules on Antigen Presenting Cells", *Israeli Immunol. Soc.,* May 3-4, 1994 (Abstract).

Fridkis-Hareli, et al., "Synthetic Copolymer 1 and Myelin Basic Protein do no Require Processing Prior to Binding to Class II Major Histocompatibility Complex Molecules on Living Antigen Presenting Cells", *Department of Chemical Immunology, The Weizmann Institute of Science,* Rehovot, Israel, 1994.

Fridkis-Hareli, et al., "Synthetic Copolymer 1 and Myelin Basic Protein Do Not Require Processing Prior to Binding to Class II Major Histocompatibility Complex Molecules on Living Antigen-Presenting Cells", *Cell. Immunol.,* 1995, 163, 229-236.

Jacobs, et al., "Advances in Specific Therapy for Multiple Sclerosis", *Neurol.,* 1994, 7, 250-254.

Johnson, "Experimental Therapy of Relapsing-Remitting Multiple Sclerosis with Copolymer-1", *Ann. Neurol.,* 1994, 36,(Suppl.), 115-117.

Kott, et al., "COP-1 Increases Suppressor Cells Number in Multiple Sclerosis", *Israel Neurological Assoc.,* Dec. 19-20, 1994, Herzliya (Israel), 17.

Mengle-Gaw, "The Major Histocompatibility Complex (MHC)", in *Encycl, Molecular Bio.* (Oxford Blackwell Science Ltd, 1994) 602-606.

Milo, et al., "Additive Effects of COP-1 and IFN-Beta on Immune Responses to Myelin Basic Protein", *Neurol.*, 1994, 44(Suppl. 2), A212.

Milo, et al., "Additive Effect of Copolymer-1 and Interferon-β on the Immune Response to Myelin Basic Protein", *Assaf Harofeh Medical Center, Sackler School of Medicine, Tel-Aviv University of Maryland School of Medicine*, 1994, 22.

U.S. Appl. No. 09/405,743, filed Sep. 24, 1999, Gad et al.

U.S. Appl. No. 09/768,872, filed Jan. 23, 2001, Aharoni et al.

U.S. Appl. No. 09/816,989, filed Mar. 23, 2001, Gad et al.

U.S. Appl. No. 09/885,227, filed Jun. 20, 2001, Moses et al.

U.S. Appl. No. 09/487,793, filed Jan. 20, 2000, Eisenbach-Schwartz et al.

U.S. Appl. No. 09/620,216, filed Jul. 20, 2000, Eisenbach-Schwartz et al.

Milo, et al., "Copolymer-1 and Interferon-β Additively Suppress the Immune Response to Myelin Basic Protein by Inhibiting Antigen Presentation", *J. Neuroimmunol.*, 1994, 54, 183 (Abstract).

Nightingale, et al., "Access to Investigational Drugs for Treatment Purposes", *Am. Family Physician*, 1994, 50(4), 845-847.

Schlegel, et al., "Prevention of Graft-Versus-Host Disease by Peptides Binding to Class II Major Histocompatibility Complex Molecules", *Blood*, 1994, 84(8), 2802-2810.

Stark, "Expanded Clinical Trials of Treatments for Multiple Sclerosis (MS): Copolymer 1 (COP-1) Treatment Investigational New Drug (IND) Program", *Ann. Neurol.*, 1994, 36, 114-115.

Teitelbaum, et al., "Immunological Parameters in a Multicenter Clinical Trial of COP1 in Multiple Sclerosis (MS): A 2-year Follow-up", *Neurol.*, 1994, 44(Suppl. 2), A358.

Tisch et al., "Antigen-specific immunotherapy: Is it a Real Possibility to Combat T-Cell-Mediated autoimmunity?" *Proc. Natl. Acad. Sci. U.S.A.*, 1994, 91, 437-438.

Milo, et al., "Additive Effects of Copolymer-1 and Interferon β-1 b on the Immune Response to Myelin Basic Protein", *J. Neuroimmunol.*, 1995, 61, 185-193.

O'Connor, et al., " Powders" in *The Science and Practice of Pharmacy*,Remington, 1995, 2, 1598-1614.

Porter, "Coating of Pharmaceutical Dosage Forms," in *The Science and Practive of Pharmacy*, Remington, 1995, 2, 1650-1659.

Reilly, Jr., W.J., "Pharmaceutical Necessities" in *The Science and Practice of Pharmacy*, Remington, 1995, 2, 1380-1416.

Schlegel, et al., "Inhibition of Allorecognition and Prevention of Graft-vs-host Disease (GVHD) by GLAT, a Synthetic Polymer with Promiscuous Binding to Murine and Human MHC Class II Molecules", in *Am. Soc. Hematology, 37th Annual Meeting*, Seattle, WA (USA), Dec. 1-5, 1995, 224a (Abstract).

Ben-Nun, et al., "The Autoimmune Reactivity to Myelin Oligodendrocyte Glycoprotein (MOG)in Multiple Sclerosis is Potentially Pathogenic: Effect of Copolymer 1 on MOG-induced Disease", *J. Neurol.*, 1996, 243(Suppl. 1), S14-S22.

U.S. Appl. No. 09/765,301, filed Jan. 22, 2001, Eisenbach-Schwartz et al.

U.S. Appl. No. 09/765,644, filed Jan. 22, 2001, Eisenbach-Schwartz et al.

Johnson, Management of Relapsing/Remitting Multiple Sclerosis with Copolymer 1 (Copaxone), *Chemical Abstracts*, 1996, 125, 291993b.

Sykes, "Immunobiology of Transplantation", *Faseb J.*, 1996, 10, 721-730.

Teitelbaum, et al., "Copolymer 1 Inhibits Chronic Relapsing Experimental Allergic Encephalomyelitis Induced by Proteolipid Protein (PLP) Peptides in Mice and Interfaces with PLP-specific T Cell Responses", *J. Neuroimmunol.*, 1996, 64, 209-217.

Aharoni, et al., "Studies on the Mechanism and Specificty of the Effect of the Synthetic Random Copolymer GLAT on Graft-versus-Host Disease", *Immunol. Letters*, 1997, 58, 79-87.

Puri et al., "Modulation of the Immune Response in Multiple Sclerosis"*J. Immunol.*, 1997, 158, 2471-2476.

Tarcic et al., "Copolymer 1 (Copaxone) from an Idea to a Drug for Treatment of Multiple Sclerosis" Database HCAPLUS on STN, Israel: AN 1997:333270. Kim, Handasa Kim, 1997, 281(14), 16-18 (Abstract).

Teitelbaum, et al., "Copolymer 1 from the Laboratory to FDA", *Israel J. Med. Sci.*, 1997, 33, 280-284.

Fridkis-Hareli, et al., "Promiscuous Binding of Synthetic Copolymer 1 to Purified HLA-DR Molecules" *J. Immunol.*, 1998, 160, 4386-4397.

Fridkis-Hareli, et al., "Synthetic Amino Acid Copolymers that Bind to HLA-DR Proteins and Inhibit Type II Collagen-reactive T Cell Clones", *Proc. Natl. Acad. Sci.*, Oct. 1998, 95, 12528-12531.

Cazzato, et al., "Treatment of Multiple Sclerosis. The Present and the Future. Study Group on Diagnosis and Therapy of Multiple Sclerosis", Database Medline on STN, Instituto do Clinica Neurologica, Università, Trieste, Italy: Medline AN: 2000060325, Recent Progressi in Medicina. Oct. 1999,90(10), 538-544 (Abstract).

Kepsutlu et al., "Evaluation of Chitosan Used as an Excipient in Tablet Formulations", Database HCAPLUS on STN, Department of Pharmaceutical Technology, Gulhane Military Medical Academy, Ankara, 06018, Turkey, HCAPLUS AN: 1999: 590411, Acta. Pol. Pharm. 1999, 56(3), 227-235 (Abstract).

Prat, et al., "Lymphocyte Migration and Multiple Sclerosis: Relation with Disease Course and Therapy," *Ann. Neurol.*, 46, 253-256 (1999).

Fridkis-Hareli et al., "Synthetic Peptides that Inhibit Binding of the Collagen Type II 261-273 Epitope to Rheumatoid Arthritis-Associated HLA-DRI and DR4 Molecules and Collagen-Specific T-cell Responses", Database HCAPLUS on STN, Department of Clinical Immunology, Aarbus University Hospital, Aarhus, Denmark, HCAPLUS AN: 2000:455053, Human Immunology, 2000, 61(7), 640-650 (Abstract).

Durelli, "Immunotherapeutics of Multiple Sclerosis", *Instituto di Clinica delle Malattie del Sistema Nervoso Universita di Torino*, 467-475.

Henry, Celia M., "Special Delivery", *Chem. and Eng. News*, Sep. 18, 2000, 49-54.

Cohen, "Fundamental Immunology", *Systemic Autoimmunity*, 4th Ed., 1999, 1083.

Fridkis-Hareli et al., "Binding of random copolymers of three amino acids to class II MHC molecules", *Intl. Immunol.*, 1999, 11(5): 635-641.

Li et al., "Glatiramer acetate blocks the activation of THP-1 cells by interferon-γ", *Eur. J. Pharmacol.*, 1998, 342: 303-310.

Zisman et al., "Dichotomy between the T and the B cellepitopes of the synthetic polypeptide (T,G)-A--L", *Eur. J. Immunol.*, 1994, 24(10): 2497-2505 (Abstract).

Deeb et al., "Comparison of Freund's and Ribi adjuvants for inducing antibodies to the synthetic antigen (TG)-AL in rabbits", *J. Immunol. Methods*, 1992, 152(1): 105-113 (Abstract).

Zisman et al., "Direct binding of a synthetic multichain polypeptide to Class II Major Histocompatibility Complex molecules on Antigen-Presenting Cells and stimulation of a specific T-cell line require processing of the polypeptide", *Proc. Natl. Acad. Sci. USA*, 1991, 88(21): 9732-9742 (Abstract).

Matsunaga et al., "Complementation of Class II A alleles in the immune response to (Glu-Lys-Tyr) polymers", *Yokohama Med. Bull.*, 1988, 39(1-2): 9-19 (Abstract).

De Kruyff et al., "Analysis of T Cell Responses to Poly-L (GluLys) at the Clonal Level. I. Presence of Responsive Clones in Nonresponder Mice", *Eur. J. Immunol.*, 1987, 17 (8); 1115-1120 (Abstract).

Lai et al., "Complementation of Class II A alleles in the immune response to (GluLysTyr) polymers", *Exp. Clin. Immunogenet.*, 1986, 3(1): 38-48 (Abstract).

Lai et al., "Monoclonal T cell responses to two epitopes on a single immunogen controlled by two distinct genes", *J. Immunol.*, 1986, 136(10): 3799-3804 (Abstract).

Trannoy et al., "Epitope-specific regulation of the T cell repertoire: carrier recognition in association with I-E or I-A does not influence the restriction of hapten-specific T cells", *Eur. J. Immunol.*, 1985, 15(12): 1215-1221 (Abstract).

Falo et al., "Analysis of antigen presentation by metabolically inactive accessory cells and their isolated membranes", *Proc. Natl. Acad. Sci. USA*, 1985, 82(19): 6647-6651 (Abstract).

Babu et al., "Ir gene control of T and B Cell Repsonses to Determinants in (Glu Lys Ala) Terpolymer", *J. Immunogenet.*, 1984, 11(3-4): 251-254.

Babu et al., "Reevaluation of response patterns of nonresponder mice to GLPhe polymers", *Immunogen.*, 1983, 18(1): 97-100 (Abstract).

Herzenberg et al., "Lack of immune response gene control for induction of epitope-specific suppression by TGAL antigen", *Nature*, 1982, 295: 329-331.

Baxevanis et al., "Genetic Control of T-Cell Proliferative Responses to Poly (Glu$^{40}$Ala$^{60}$) and Poly (Glu$^{51}$Lys$^{34}$Tyr$^{15}$): Subregion-Specific Inhibition of the Responses with Monoclonal Ia Antibodies", *Immunogenetics*, 1980, 11; 617-628.

Maurer et al., "Interpretations of immune responses of mice to poly(Glu60Lys40), its modified derivatives, and the terpolymers poly (Glu55Lys37Leu8) and poly (Glu56Lys37Ser7)", *Clin. Immunol. Immunopathol.*, 1980, 15(3): 344-356 (Abstract).

Ju et al., "Idiotypic analysis of antibodies against the terpolymer L-glutamic acid 60-L-alanine30-L-tyrosine10 (GAT). IV. Induction of CGAT idiotype following immunization with various synthetic polymers containing glutamic acid and tyrosine", *Eur. J. Immunol.*, 1979, 9(7): 553-560 (Abstract).

Schwartz et al., "Gene complementation in the T lymphocyte proliferative response to poly (Glu57Lys38Tyr5): Evidence for effects of polymer handling and gene dosage", *J. Immunol.*, 1979, 123(1): 272-278 (Abstract).

Kropshofer et al., "Self-Peptides from Four HLA-DR Alleles Share Hydrophobic Anchor Residues Near the NH$_2$- Terminal Including Proline as a Stop Signal for Trimming", *J. Immunol.*, 1993, 151: 4732-47472.

Harrison and Hafler, "Antigen-Specific Therapy for Autoimmune Disease", *Current Opin. Immunol.*, 2000, 12(6): 704-711.

Pender et al. *Int. Med. Journal*, 2002, 32: 554-563.

Van Noort et al., *International Review of Cytology*, 1995, 178: 127-205.

Webster's II New Reiverside University Dictionary, The Riverside Publishing Company, 1984, 933.

Aharoni, et al., "Copolymer I induces T cells of the T helper type 2 that crossreact with myelin basic protein and suppress experimental autoimmune encephalomyelitis", *Proc. Natl. Acad. Sci. USA*, 1997, 94, 10821-10826.

Aharoni, et al., "Cop 1 Specific Supporessor Cells Inhibit Experimental Allergic encephalomyelitis Induced by Either Mouse Spinal Cord Homogenate or Proteolipid Protein Peptide 139-151", Neurology, 1997 vol. 48, No. 3, A422.

Aharoni, et al., "Bystander Suppression of Experimental Autoimmune Encephalomyelitis by T Cell Lines and Clones of the Th2 Type Induced by Copolymer I", *J. Neuroimmunol.* 1998, 91(1-2), 135-146.

Asakura et al., "Aunique population of circulating autoantibodies promotes central nervous system remyelination", *Multiple Sclerosis*, 1998, 4, 217-221.

Asakura et al., "Targeting o f 1gMk Antibodies to Oligodendrocytes Promotes CNS Remyelination", *The Journal of Neuroscience*, 1998, (19), 1700-1108.

Bieber, et al., "Antibody-mediated remyelination: relevance to multiple sclerosis", *Multiple Sclerosis*, 2000, 6(2), S1-S5.

Bieber, et al., "Humoral autoimmunity as a mediator of CNS repair", *A Trends Guide to Neurodegenerative Disease and Repair/Review*, 2001, 24(11), S39-S44.

Duda, et al., "Human and Murine CD4 T Cell Reactivity to a Complex Antigen: Recognition of the Synthetic Random Polypeptide Glatiramer Acetate", The Journal of Immunology, 2000, 165, 7300-7307.

Johnson, et al. "Copolymer 1 reduces relapse rate and improves disability in relapsing-remitting multiple sclerosis: results of a phase III multicenter, double-blind placebo-controlled trial. The Copolymer 1 Multiple Sclerosis Study Group", Neurology, 45(7), 1268 (abstract).

Lovell, K. and Jones, M., "CNS Infections, Spongiform Encephalophathy and Demyelinating Diseases," Karol Marcinkowski U. Med. Sci., Dept. Pathol., Poland [online] [retrieved on Apr. 19, 2003]. Retrieved from internet: <URL: http://ampat.amu.edu.pl/guzyuno/ CNS_INFE.HTM>.

McGavern, et al. "Do Antibodies Stimulate Myelin Repair in Multiple Sclerosis!", The Neuroscientist, 1999, 5(1), 19-28.

*Merck Manual of Diagnosis and Therapy*, Merck Research laboratories, Whitehouse Station, N.J., 17$^{th}$ Ed., 1999, 1300-1303, 1312-1317.

Pavelko, et al., "Acceleration in the Rate of CNS Remyelination in Lysolecithin-Induced Demyelination", *The Journal of Neuroscience*, 1998 18(7), 2498-2505.

Pharmacia Biotech Directory, 1996, pp. 340-341.

Physician's Desk Reference, 2000, Medical Economics Co. Inc., Montvale, NJ, 3115.

Rodriguez, et al., *Neurological Therapeutics*, 15(3): 245-250.

Teva, et al., "Copolymer-I Glatiramer Acetate Copaxane Agent for Multiple Sclerosis", Drugs of the Future, 1998, vol. 23, No. 2, 213-214.

Warrington, et al., "Human monclonal antibodies reactive to oligodenrocytes promote remyelination in a model of multiple sclerosis", PNAS, 2000, 97(12), 6820-6825.

Warrington, et al., "Immunoglobulin-mediated CNS repair", J. Allergy Clin. Immunol., 2001, S121-S125.

Wiesemann, et al., "Glatiramer Acetate (GA) induces IL-13/IL-5 secretion in naïve T cells", Journal of Neuroimmunology, 2001, 119, 137-144.

Lampert, et al., "Expression of Matrix Matalloproteinases and Their Inhibitors in Human Brain Tumors", American Journal of Pathology, vol. 153, No. 2, 1998, 429-437.

Pereira, et al., "The Blood-Brain Barrier in HIV-associated Dementia", NeuroAcids, vol. 3, No. 2, 2000.

Kieseier, et al., "Differential Expression of Matrix Matalloproteinases in Bacterial Menigitis", Brain, 1999, 122: 1579-1587.

* cited by examiner

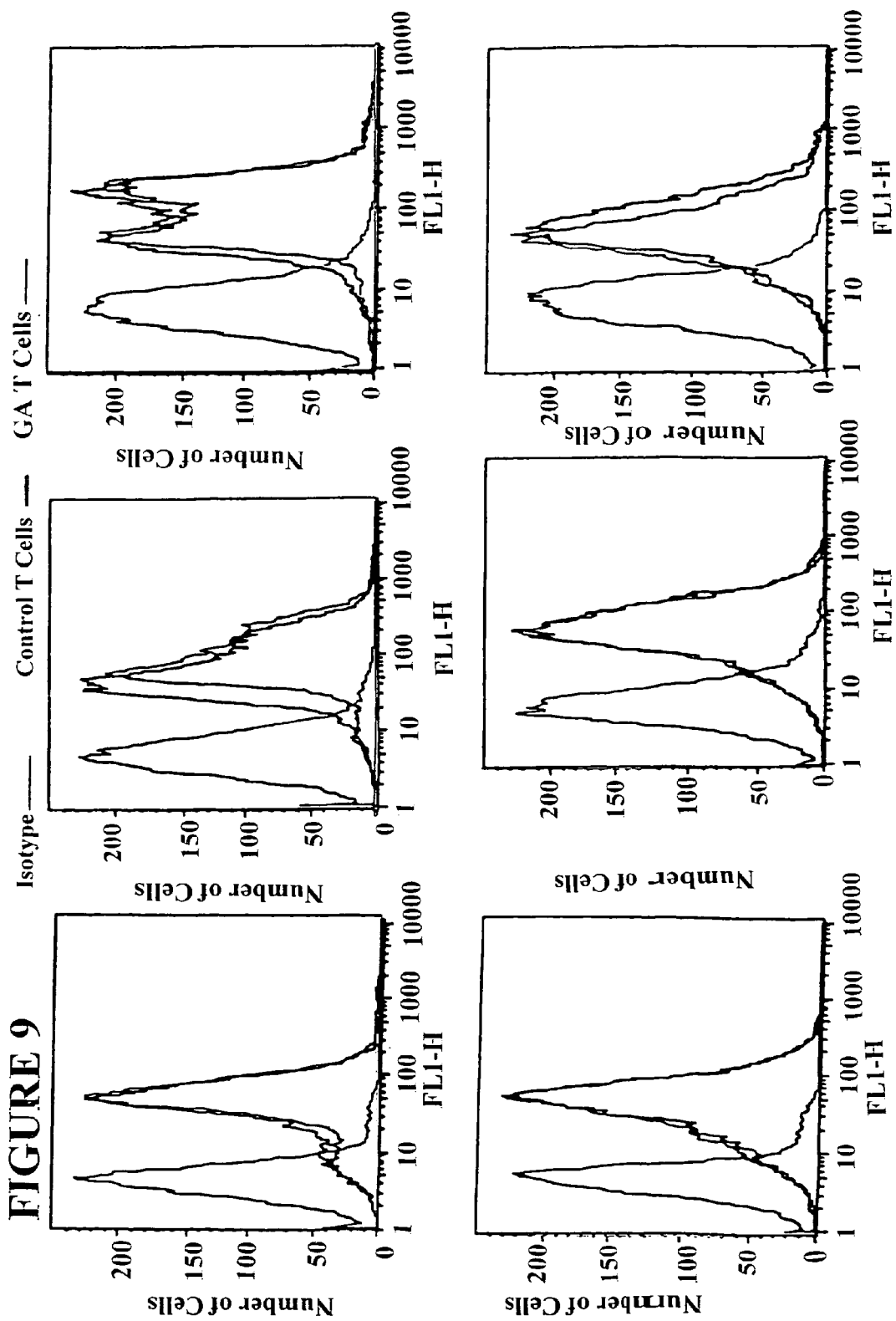

US 7,033,582 B2

USE OF GLATIRAMER ACETATE (COPOLYMER 1) IN THE TREATMENT OF CENTRAL NERVOUS SYSTEM DISORDERS

The present application is a continuation of U.S. Ser. No. 09/875,429, filed Jun. 5, 2001 now abandoned, which claims the benefit of U.S. Provisional Application No. 60/209,372, filed Jun. 5, 2000, which is incorporated by reference herein.

Throughout this application, various references are cited, using arabic numbers within parentheses. Full citations for these references can be found at the end of the specification, immediately preceding the claims. These publications, in their entireties, are hereby incorporated by reference into the application to more fully describe the state of the art to which the invention pertains.

FIELD OF THE INVENTION

The present invention provides methods of treating a mammalian subject having, or genetically predisposed to, an inflammatory, non-autoimmune central nervous system (CNS) disease, or alleviating the symptoms of such a disease.

BACKGROUND

The nervous system of vertebrates is divided into the central nervous system, comprised of the brain and spinal cord, and the peripheral nervous system, consisting of the outlying nerves (22). The axons of most nerve cells are covered with a myelin sheath, a stack of specialized plasma membranes. Glial cells that wrap around the axons produce the myelin sheath. In the CNS, these glial cells are called oligodendrocytes. Each region of myelin formed by an individual oligodendrocyte is separated from the next region by an unmyelinated area called the node of Ranvier (22).

The myelin sheath acts as an electric insulator of the axon and all electric activity in axons is confined to the nodes of Ranvier.

One of the more common types of CNS diseases among human adults is multiple sclerosis. This condition is a demyelinating disease. Multiple sclerosis is a chronic, frequently progressive, inflammatory CNS disease characterized pathologically by primary demyelination and axonal injury. In multiple sclerosis patients, conduction of action potentials by the demyelinated neurons is slowed (22). Even though the etiology of multiple sclerosis is unknown, several immunological features of multiple sclerosis, and its moderate association with certain major histocompatibility complex alleles, has prompted the speculation that multiple sclerosis is an immune-mediated disease (17, 33, 55). An autoimmune hypothesis is supported by the experimental autoimmune (allergic) encephalomyelitis (EAE) model, where the injection of certain myelin components into genetically susceptible animals leads to T lymphocyte-mediated CNS demyelination (58).

Some researchers view activated T lymphocytes as a trigger of multiple sclerosis. They postulate that once T lymphocytes traverse the blood brain barrier (BBB) into the CNS parenchyma, they are reactivated following antigen presentation by microglia (53). The entry of leukocytes into tissues is a multi-step process that includes adhesion onto endothelial cells and transmigration across the endothelial barrier.

Recent evidence suggests that the expression of matrix metalloproteinases (MMPs) by leukocytes is required for T lymphocytes to enter the CNS parenchyma (42, 77, 88). An MMP is a proteolytic enzyme that possesses an active site where an invariant zinc binds to cysteine residues in the propeptide region of the MMP, keeping the MMP in an inactive state (50, 89). Activating agents disrupt the cysteine-zinc interaction to expose the active site so that catalysis can occur.

The inappropriate expression of MMPs is speculated to be involved in the pathogenesis of malignant gliomas, stroke and Alzheimer's disease. Furthermore, several lines of evidence suggest a role for MMPs in the disease process in multiple sclerosis (37, 91). In this regard, immunohistochemically identified MMPs (specifically MMP-3, -7, -9 and -12), on microglia, astrocytes and infiltrating leukocytes, have now been documented by several groups to be present in the autopsied brains of multiple sclerosis subjects (4, 18, 21, 47, 57) and in the brains of EAE animals (16, 37). Analyses of serum samples reveal levels of MMP-9 to be significantly increased in multiple sclerosis patients compared to healthy controls; within the multiple sclerosis population, serum MMP-9 levels are higher during clinical relapse relative to periods of stability (40). In addition, serum MMP-9 levels are correlated with the number of gadolinium-enhancing lesions detected by magnetic resonance imaging (MRI) (40, 84).

In correspondence with a pathogenic role of MMPs, several hydroxamate-based agents developed to inhibit the activity of MMPs (e.g. GM6001, Ro31-9790 and BB-1101) were found to alleviate the incidence and severity of EAE (32, 34, 43, 52).

A prominent method of microglia activation is believed to be a non-antigen-specific interaction between these cells and T lymphocytes, which generates cytokines within the CNS milieu (19, 20, 67). This contention is supported by several findings obtained in culture studies. For instance, human T lymphocytes and human microglia interact to generate significant amounts of TNF-α and IL-10 (14, 15). The effect of T lymphocytes on microglia is equipotent to that of lipopolysaccharide, a very effective microglia stimulator. Researchers found additional support in the observation that the interaction between T lymphocytes and microglia does not require antigen or MHC restriction. Experiments have also shown that in a facial nerve resection model in mouse, T cells infiltrated the CNS and aggregated around microglia, and that this was correspondent with an increase in IL-1β and TNF-α (61). In a graft-versus-host disease (GVHD) model, activated microglial cell clusters were invariably intimately associated with T cell infiltrates (68).

TNF-α can influence lymphocyte trafficking across endothelium by up regulating the expression of various adhesion molecules involved in this process (76), and is implicated in the process of demyelination. Indeed, TNF-α directly induces in vitro the apoptotic death of the myelin-producing cells in the brain, the oligodendrocytes (26, 45, 71), and intravitreal injection of TNF-α causes demyelination of mouse optic nerve axons (12). In addition, TNF-α is pro-inflammatory. The level of TNF-α is found to be elevated in the serum, cerebrospinal fluid, and brain lesions of multiple sclerosis patients, and is correlated with the disease activity (13, 35, 62, 72). TNF-α is also implicated in the pathogenicity of EAE—the administration of antibodies to TNF-α or soluble TNF-α receptors prevents the transfer of EAE and abrogates autoimmune demyelination (63, 69, 70).

IL-12 is another pro-inflammatory cytokine which has a key role in switching uncommitted T lymphocytes to the pro-inflammatory Th1 subset which secretes IFN-γ and TNF-α/β (91). IL-1β also promotes an inflammatory response and has been associated with multiple sclerosis (66).

The Th2 subset produces IL-4, IL-10 and IL-13, regulates humoral immunity and decreases local inflammation. Both IL-4 and IL-10 can inhibit the differentiation of naive precursors into Th1 cells (91). IL-4 promotes the activation of B lymphocytes and macrophages and also stimulates class switching of antibodies (22).

IL-13 is a Th2 cytokine with important immunomodulating activities. The best known IL-13 mediated function is its ability to drive the differentiation of naive CD4+ T cells towards a Th2 phenotype (75). The anti-inflammatory functions of IL-13 include the suppressive effect on the production of pro-inflammatory cytokines by activated monocytes or by alveolar macrophages (81), the induction of 15-lipoxygenase (51) and the inhibition of prostaglandin E2 (PGE2) formation (27). Functions of IL-13 in the CNS and on glial cell functions are not well defined (87).

IL-10 is an anti-inflammatory cytokine produced by a variety of cells, including monocytes/macrophages, T lymphocytes, and mast cells. In the CNS, potential sources of IL-10 include microglia (86) and astrocytes (49). IL-10 has important anti-inflammatory properties. First, IL-10 inhibits the production of proinflammatory cytokines by many cell types, including those of the mononuclear phagocytic lineage; indeed, IL-10 was shown to inhibit the production of TNF-α and IL-12 produced by monocytes, macrophages, and microglia (3, 9, 10, 24, 38). Also, IL-10 plays a role in causing T lymphocytes to undergo anergy (inactivation or unresponsiveness) (2). Other anti-inflammatory functions of IL-10 include its inhibitory effect on the process of antigen presentation. Treatment of macrophages/microglia with IL-10 down-regulated the expression of molecules essential for presentation of antigens, such as MHC class II (24) and the costimulatory molecules B7-1 and B7-2 (36). Finally, the role of IL-10 as an anti-inflammatory molecule is supported by the phenotype of IL-10-deficient mice; these mice develop chronic colitis, which appears to be mediated by the proinflammatory Th1 cells (8, 23, 39).

The afore-mentioned cytokines are inducible, meaning that they are produced in response to certain stimuli. In contrast, IL-6, which activates B-lymphocytes (22), is constitutive.

SUMMARY OF THE INVENTION

The subject invention provides a method of treating a mammalian subject having an inflammatory, non-autoimmune central nervous system (CNS) disease, or alleviating the symptoms of such a disease, comprising administering glatiramer acetate (Copolymer 1) to the subject in an amount and for a duration of time effective to treat the inflammatory, non-autoimmune CNS disease.

The subject invention also includes a method of treating a mammalian subject at risk of developing an inflammatory, non-autoimmune CNS disease comprising administering glatiramer acetate (Copolymer 1) to the subject in an amount and for a duration of time effective to minimize the severity of the inflammatory, non-autoimmune CNS disease that may occur in the subject or prevent its occurrence.

Further encompassed by the subject invention is a method of inhibiting the activity of a matrix metalloproteinase comprising contacting the matrix metalloproteinase with glatiramer acetate (Copolymer 1).

In addition, the subject invention contains a method of suppressing the production of a cytokine by activated T lymphocytes comprising contacting the activated T lymphocytes with glatiramer acetate (Copolymer 1) in an amount necessary to suppress cytokine production.

The subject invention also provides the use of glatiramer acetate (Copolymer 1) in the preparation of a pharmaceutical composition for the treatment of an inflammatory, non-autoimmune central nervous system (CNS) disease, or alleviation of the symptoms of such a disease, wherein said pharmaceutical composition is administered to the subject in an amount and for a duration of time effective to treat the inflammatory, non-autoimmune CNS disease in a mammalian subject.

The subject invention further concerns the use of glatiramer acetate (Copolymer 1) in the preparation of a pharmaceutical composition for treating a mammalian subject at risk of developing an inflammatory, non-autoimmune CNS disease, wherein said pharmaceutical composition is administered to the subject in an amount and for a duration of time effective to minimize the severity of the inflammatory, non-autoimmune CNS disease that may occur in the subject or prevent its occurrence.

In addition, the subject invention includes the use of glatiramer acetate (Copolymer 1) in the preparation of a pharmaceutical composition for inhibiting the activity of a matrix metalloproteinase.

The subject invention also provides the use of glatiramer acetate (Copolymer 1) in the preparation of a pharmaceutical composition for suppressing the production of a cytokine by activated T lymphocytes.

BRIEF DESCRIPTION OF THE FIGURES

FIG. 2-A shows MMP-9 (the strongest band) from Baby Hamster Kidney (BHK) cells while FIG. 2-B represents MMP-9 produced by T lymphocytes.

FIG. 3-A demonstrates that 25 μg/ml Copolymer 1 treatment of T lymphocytes, for 1, 2 or 3 days, did not affect the subsequent migration of cells across a fibronectin barrier compared to controls. In contrast, 3 days treatment of cells with IFNβ-1b (1000 IU/ml) decreased migration by 20–50% as reported previously (77). In FIG. 3-B, 3-day pretreatment of T lymphocytes with various concentrations of Copolymer 1 similarly did not affect transmigration. Values are mean±SEM of 3 analyzes each, and have been expressed as % of controls of the respective dose-response experiments.

FIG. 8-A shows that adult human microglia are mostly bipolar in morphology in culture. FIG. 8-B demonstrates that T lymphocytes are present as single cells or clumps. FIG. 8-C reports that when T lymphocytes are co-cultured with microglia in the absence of Copolymer 1, bipolar microglia become rounded/ameboid in morphology (some microglia are shown by arrows). As FIG. 8-D reflects, this morphological transformation is prevented by Copolymer 1 pretreatment of T lymphocytes (some bipolar microglia are indicated by arrows). All figures portray the same magnification, 400×.

FIG. 9 reports that Copolymer 1 does not affect CXCR3 and CXCR4 expression on T lymphocytes. All T lymphocytes were activated at time 0 with anti-CD3 antibody and Copolymer 1 (25 ug/ml) was added to some cultures at 3 hours. Cells were removed and stained at 1 (FIGS. 9-A and 9-B), 2 (FIGS. 9C and 9-D) and 3 days (FIGS. 9-E and 9-F). An isotype control antibody was used to stain control or Copolymer 1-treated T lymphocytes and the fluorescence of these did not differ. Thus, only the isotype staining for control T lymphocytes is displayed.

DETAILED DESCRIPTION OF THE INVENTION

Figure 1:
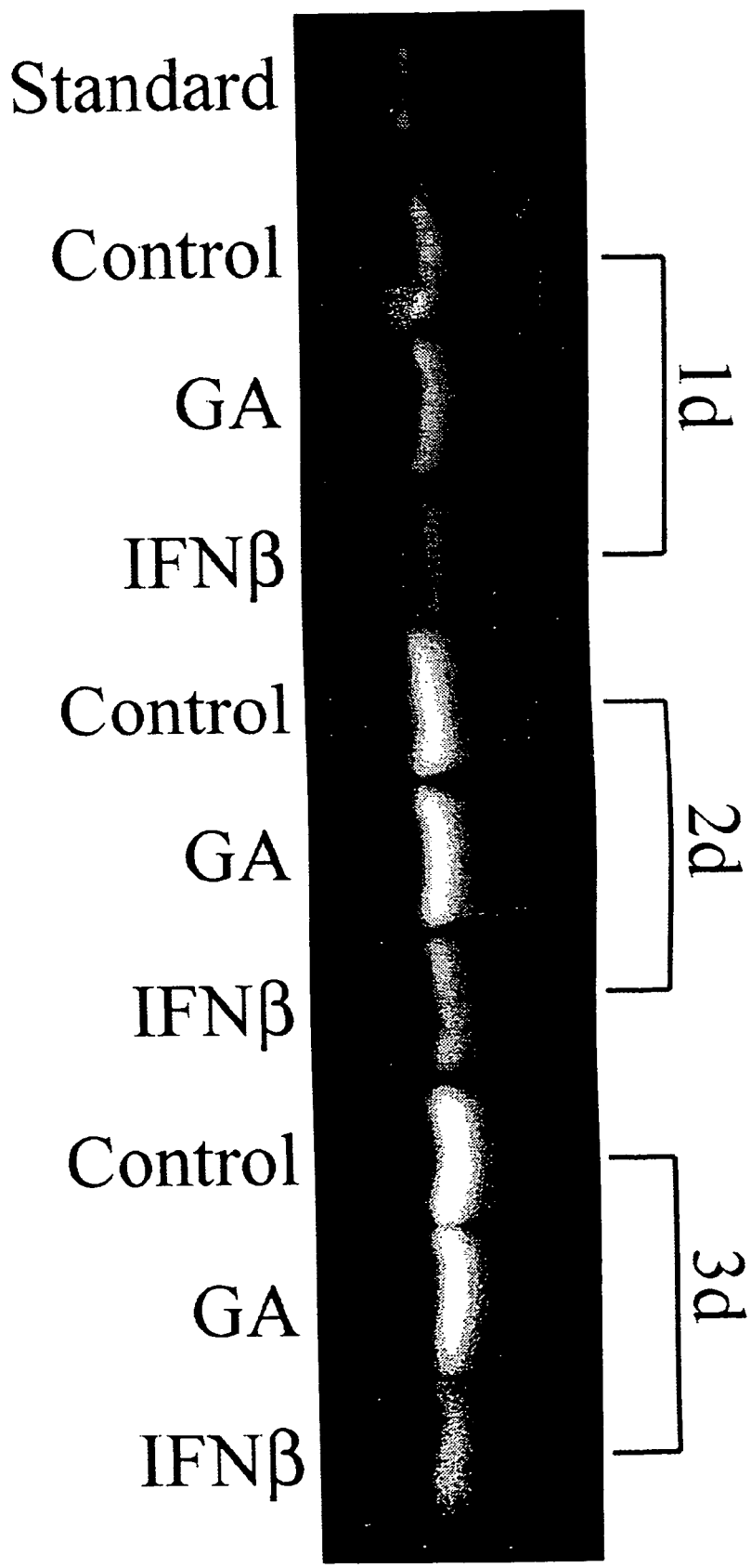
FIG. 1 shows the lack of effect of Copolymer 1 (glatiramer acetate (GA)) on MMP-9 production by T lymphocytes. AIM-V conditioned media were collected from anti-CD3 activated T lyphocytes either in the absence of any drug treatment (control) or in the presence of 25 μg/ml Copolymer 1 or 1000 IU/ml recombinant interferon β-1b. Interferon β (IFN-β) inhibited T lymphocyte production of MMP-9, as previously reported (77), but Copolymer 1 did not affect MMP-9 protein levels. Similar results were obtained from monocytes after 1 day of treatment. The conditioned media at each time point were collected from cultures with equivalent amounts of T lymphocytes.

A non-autoimmune disease refers to a condition characterized by a lack of significant immune-mediated damage to the diseased subject.

Oftentimes, an inflammatory disease is characterized as a condition in which there is increased blood flow to the affected areas, resulting in swelling and heightened temperature, which may produce pain.

As used in this application, an inflammatory, non-autoimmune disease includes any disease which impacts the central nervous system, but does not include an autoimmune component and is associated with an inflammatory response in the subject afflicted with the disease. Inflammatory, non-autoimmune diseases include, inter alia, Alzheimer's disease, Parkinson's disease, HIV encephalopathy, brain tumor, glaucoma, neuropathy, dementia, central nervous system infection, central nervous system bacterial infection, meningitis, stroke, and head trauma.

The subject invention encompasses a method of treating a mammalian subject having an inflammatory, non-autoimmune central nervous system (CNS) disease, or alleviating the symptoms of such a disease, comprising administering glatiramer acetate (GA or Copolymer 1) to the subject in an amount and for a duration of time effective to treat the inflammatory, non-autoimmune CNS disease.

In one embodiment, the mammalian subject is human.

In another embodiment, the disease is Alzheimer's Disease.

In a further embodiment, the disease is Parkinson's Disease.

In yet another embodiment, the disease is HIV encephalopathy.

In a further embodiment, the disease is a brain tumor.

In another embodiment, the disease is glaucoma.

In a further embodiment, the disease is neuropathy or dementia.

In another embodiment, the disease is a CNS infection.

In one embodiment, the CNS infection is a bacterial infection.

In another embodiment, the bacterial infection is meningitis.

In a further embodiment, the disease results from stroke.

In yet another embodiment, the disease results from head trauma.

The subject invention encompasses embodiments wherein the route of administration is oral, intravenous, intramuscular, subcutaneous, intraperitoneal, transdermal, nasal or rectal. The preferred routes of administration are oral and subcutaneous injection.

In one embodiment, the dose of glatiramer acetate (Copolymer 1) administered ranges from about 0.1 mg to about 1000 mg.

In another embodiment, the dose of glatiramer acetate (Copolymer 1) administered ranges from about 1 mg to about 100 mg.

In a further embodiment, the dose of glatiramer acetate (Copolymer 1) administered ranges from about 5 mg to about 50 mg.

In yet another embodiment, the dose of glatiramer acetate (Copolymer 1) administered ranges from about 10 mg to about 30 mg.

In one embodiment, the dose of glatiramer acetate (Copolymer 1) administered is about 20 mg.

In another embodiment, the dose of glatiramer acetate (Copolymer 1) administered ranges from about 0.05 mg/kg of body weight to about 50 mg/kg of body weight.

In a further embodiment, the dose of glatiramer acetate (Copolymer 1) administered ranges from about 0.1 mg/kg of body weight to about 10 mg/kg of body weight.

In an additional embodiment, the dose of glatiramer acetate (Copolymer 1) administered ranges from about 0.1 mg/kg of body weight to about 1.0 mg/kg of body weight.

In another embodiment, the dose of glatiramer acetate (Copolymer 1) administered is about 0.3 mg/kg of body weight.

In one embodiment, the dose of glatiramer acetate (Copolymer 1) is administered at a frequency of about once every 30 days to about once every day. In a preferred embodiment, the dose of glatiramer acetate (Copolymer 1) is administered at a frequency of about once every 7 days to about once every day. In a more preferred embodiment, the dose of glatiramer acetate (Copolymer 1) is administered at a frequency of about once every day.

In another embodiment, the glatiramer acetate (Copolymer 1) is administered as part of a therapeutic regimen during which a cytokine antagonist is also administered to the subject.

The subject invention also concerns a method of treating a mammalian subject at risk of developing an inflammatory, non-autoimmune CNS disease comprising administering glatiramer acetate (Copolymer 1) to the subject in an amount and for a duration of time effective to minimize the severity of the inflammatory, non-autoimmune CNS disease that may occur in the subject or prevent its occurrence.

In one embodiment, the subject is human and the risk is associated with a genetic predisposition to a chronic medical condition.

In another embodiment, the disease is selected from the group consisting of Alzheimer's Disease, Parkinson's Disease, glaucoma, dementia, neuropathy, stroke, and brain tumor.

In a further embodiment, the route of administration is oral, intravenous, intramuscular, subcutaneous, intraperitoneal, transdermal, nasal or rectal.

The subject invention additionally includes a method of inhibiting the activity of a matrix metalloproteinase comprising contacting the matrix metalloproteinase with glatiramer acetate (Copolymer 1).

In one embodiment, the matrix metalloproteinase is MMP-9.

In another embodiment, the matrix metalloproteinase is in a subject.

In one embodiment, the subject is human.

The subject invention further provides a method of suppressing the production of a cytokine by activated T lymphocytes comprising contacting the activated T lymphocytes with glatiramer acetate (Copolymer 1) in an amount necessary to suppress the production of the cytokine.

In one embodiment, the cytokine is IL-1.

In another embodiment, the cytokine is IL-4.

In a further embodiment, the cytokine is IL-6.

In yet another embodiment, the cytokine is IL-10.

In a further embodiment, the cytokine is IL-12.

In another embodiment, the cytokine is IL-13.

In a further embodiment, the cytokine is TNF-a.

In one embodiment, the cytokine is in a subject.

In another embodiment, the subject is human.

The subject invention also contains the use of glatiramer acetate (Copolymer 1) in the preparation of a pharmaceutical composition for the treatment of an inflammatory, non-autoimmune central nervous system (CNS) disease, or alleviation of the symptoms of such a disease, wherein said pharmaceutical composition is administered to the subject in an amount and for a duration of time effective to treat the inflammatory, non-autoimmune CNS disease in a mammalian subject.

In one embodiment of the use, the mammalian subject is human.

In another embodiment of the use, the disease is Alzheimer's Disease.

In a further embodiment of the use, the disease is Parkinson's Disease.

In yet another embodiment of the use, the disease is HIV encephalopathy.

In a further embodiment of the use, the disease is a brain tumor.

In another embodiment of the use, the disease is glaucoma.

In a further embodiment of the use, the disease is neuropathy or dementia.

In another embodiment of the use, the disease is a CNS infection.

In one embodiment of the use, the CNS infection is a bacterial infection.

In another embodiment of the use, the bacterial infection is meningitis.

In a further embodiment of the use, the disease results from stroke.

In yet another embodiment of the use, the disease results from head trauma.

The subject invention encompasses embodiments of the use wherein the route of administration is oral, intravenous, intramuscular, subcutaneous, intraperitoneal, transdermal, nasal or rectal. The preferred routes of administration are oral and subcutaneous injection.

In one embodiment of the use, the dose of glatiramer acetate (Copolymer 1) administered ranges from about 0.1 mg to about 1000 mg.

In another embodiment of the use, the dose of glatiramer acetate (Copolymer 1) administered ranges from about 1 mg to about 100 mg.

In a further embodiment of the use, the dose of glatiramer acetate (Copolymer 1) administered ranges from about 5 mg to about 50 mg.

In yet another embodiment of the use, the dose of glatiramer acetate (Copolymer 1) administered ranges from about 10 mg to about 30 mg.

In one embodiment of the use, the dose of glatiramer acetate (Copolymer 1) administered is about 20 mg.

In another embodiment of the use, the dose of glatiramer acetate (Copolymer 1) administered ranges from about 0.05 mg/kg of body weight to about 50 mg/kg of body weight.

In a further embodiment of the use, the dose of glatiramer acetate (Copolymer 1) administered ranges from about 0.1 mg/kg of body weight to about 10 mg/kg of body weight.

In an additional embodiment of the use, the dose of glatiramer acetate (Copolymer 1) administered ranges from about 0.1 mg/kg of body weight to about 1.0 mg/kg of body weight.

In another embodiment of the use, the dose of glatiramer acetate (Copolymer 1) administered is about 0.3 mg/kg of body weight.

In one embodiment of the use, the dose of glatiramer acetate (Copolymer 1) is administered at a frequency of about once every 30 days to about once every day. In a preferred embodiment of the use, the dose of glatiramer acetate (Copolymer 1) is administered at a frequency of about once every 7 days to about once every day. In a more preferred embodiment of the use, the dose of glatiramer acetate (Copolymer 1) is administered at a frequency of about once every day.

In another embodiment of the use, the glatiramer acetate (Copolymer 1) is administered as part of a therapeutic regimen during which a cytokine antagonist is also administered to the subject.

The subject invention also concerns the use of glatiramer acetate (Copolymer 1) in the preparation of a pharmaceutical composition for treating a mammalian subject at risk of developing an inflammatory, non-autoimmune CNS disease, wherein said pharmaceutical composition is administered to the subject in an amount and for a duration of time effective to minimize the severity of the inflammatory, non-autoimmune CNS disease that may occur in the subject or prevent its occurrence.

In one embodiment of the use, the subject is human and the risk is associated with a genetic predisposition to a chronic medical condition.

In another embodiment of the use, the disease is selected from the group consisting of Alzheimer's Disease, Parkinson's Disease, glaucoma, dementia, neuropathy, stroke, and brain tumor.

In a further embodiment of the use, the route of administration is oral, intravenous, intramuscular, subcutaneous, intraperitoneal, transdermal, nasal or rectal.

The subject invention additionally includes the use of glatiramer acetate (Copolymer 1) in the preparation of a pharmaceutical composition for inhibiting the activity of a matrix metalloproteinase.

In one embodiment of the use, the matrix metalloproteinase is MMP-9.

In another embodiment of the use, the matrix metalloproteinase is in a subject.

In one embodiment of the use, the subject is human.

The subject invention further provides the use of glatiramer acetate (Copolymer 1) in the preparation of a pharmcutical composition for suppressing the production of a cytokine by activated T lymphocytes.

In one embodiment of the use, the cytokine is IL-1.

In another embodiment of the use, the cytokine is IL-4.

In a further embodiment of the use, the cytokine is IL-6.

In yet another embodiment of the use, the cytokine is IL-10.

In a further embodiment of the use, the cytokine is IL-12.

In another embodiment of the use, the cytokine is IL-13.

In a further embodiment of the use, the cytokine is TNF-a.

In one embodiment of the use, the cytokine is in a subject.

In another embodiment of the use, the subject is human.

COPAXONE® is the brand name for glatiramer acetate (formerly known as copolymer-1). Glatiramer acetate, the active ingredient of COPAXONE®, consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate is 4,700–11,000 daltons. Chemically, glatiramer acetate is designated L-glutamic acid polymer with L-alanine, L-lysine and L-tyrosine, acetate (salt). Its structural formula is:

$$(Glu, Ala, Lys, Tyr)_{x \cdot x} \cdot XCH_3COOH$$

$$(C_5H_9NO_4 \cdot C_3H_7NO_2 \cdot C_6H_{14}N_2O_2 \cdot C_9H_{11}NO_3)_x \cdot XC_2H_4O_2$$

CAS-147245-92-9 (92).

Copolymer 1 (Cop-1) can be formulated into pharmaceutical compositions containing a pharmaceutically acceptable carrier. As used herein, "pharmaceutically acceptable carrier" includes any and all solvents, adjuvants, suspending agents, emulsifying agents, dispersion media, coatings, antibacterial and antifungal agents, isotonic and absorption delaying agents, sweeteners, flavor enhancers and the like. The pharmaceutically acceptable carriers may be prepared from a wide range of materials including, but not limited to, flavoring agents, sweetening agents and miscellaneous materials such as buffers and absorbents that may be needed in order to prepare a particular oral therapeutic composition. The use of such media and agents with pharmaceutically active substances is well known in the art. Except insofar as any conventional media or agent is incompatible with the active ingredient, its use in the therapeutic compositions is contemplated.

Copolymer 1 can be formulated into any form known in the art using procedures available to one of skill in the art. Copolymer 1 may be mixed with other food forms and consumed in solid, semi-solid, suspension or emulsion form. In one embodiment, the composition is formulated into a capsule or tablet using techniques available to one of skill in the art. However, the present compositions may also be formulated in another convenient form, such as an injectable solution or suspension, a spray solution or suspension, a lotion, a gum, a lozenge, a food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, the present compositions can be formulated into cereals, snack items such as chips, bars, gum drops, chewable candies or slowly dissolving lozenges. Copolymer 1 can also be administered as dry powder or metered dose of solution by inhalation, or nosedrops and nasal sprays, using appropriate formulations and metered dosing units.

One of skill in the art can readily substitute structurally-related amino acids for Copolymer 1 without deviating from the spirit of the invention. The present invention includes polypeptides and peptides which contain amino acids that are structurally related to tyrosine, glutamic acid, alanine or lysine and possess the ability to stimulate polyclonal antibody production upon introduction. Such substitutions retain substantially equivalent biological activity in their ability to suppress or alleviate the symptoms of the CNS disease. These substitutions are structurally-related amino acid substitutions, including those amino acids which have about the same charge, hydrophobicity and size as tyrosine, glutamic acid, alanine or lysine. For example lysine is structurally-related to arginine and histidine; glutamic acid is structurally-related to aspartic acid; tyrosine is structurally-related to serine, threonine, phenylalanine and tryptophan; and alanine is structurally-related to valine, leucine and isoleucine. These and other conservative substitutions, such as structurally-related synthetic amino acids, are contemplated by the present invention.

Moreover, Copolymer 1 can be composed of l- or d-amino acids.

As is known by one of skill in the art, l-amino acids occur in most natural proteins. However, d- amino acids are commerically available and can be substituted for some or all of the amino acids used to make Copolymer 1. The present invention contemplates Copolymer 1 consisting essentially of l-amino acids, as well as Copolymer 1 consisting essentially of d-amino acids.

Experimental Details

Procedure

PBMC Isolation

Heparinized blood was collected from normal volunteers, and subjected to Ficoll-Hypaque (Pharmacia Biotech, Mississauga, Ontario) centrifugation to obtain peripheral blood mononuclear cells (PEMNCs) as described previously (15). After two washes, cells were suspended at a density of 1–2 million/ml in horizontal T-25 flasks (Nunc, Becton Dickinson, Mississauga, Ontario) in the serum free medium, AIM-V (GIBCO/BRL), to which 1 ng/ml of an anti-CD3 antibody (OKT3, compliments of Jack Antel, Montreal, Canada) was added. Three hours after the anti-CD3 addition, the T-25 flasks were stood upright from their horizontal position in order to kill monocytes that had adhered. Floating cells, which were mostly lymphocytes, were left for a period of 72 hours at 37° C. Flow cytometry analysis of the MNC population at this 72 hour period indicated that CD3+ cells constituted about 90% of the total cell population, with approximately 60% CD4+ and 30% CD8+ ratio. B lymphocytes (CD19+) and NK cells (CD56+) consisted of 5–6% of the total MNC population, and no monocytes (CD14+) were detected. Henceforth, given that the majority of cells in the MNC population are T lymphocytes, these will be referred to as T lymphocytes.

Copolymer 1 Treatment

Copolymer 1 (1–50 µg/ml) diluted in phosphate-buffered saline, was added to cultures 3 hours after the initiation of CD3 ligation, at the time that the T-25 flasks were altered from the horizontal to upright positions. Cells were left for 69 h at 37° C., then collected, counted and resuspended in fresh AIM-V at density of 500,000 cells per ml. Following a second treatment with Copolymer 1, cells were left at 37° C. for an additional 3 h. Thereafter, 500 µl (250,000 cells) of the suspension was taken for migration assays described below. Alternatively, 100 µl (50,000 cells) of cell suspension was added to each individual well of a 96-well plate already containing microglia or U937 monocytoid cells (see below). The experiments involved 72 h treatment of T lymphocytes with Copolymer 1, administered at 2 time points. The purity of T lymphocytes after 72 h of Copolymer 1 treatment was not different from that of non-treated controls. In some experiments, recombinant IFNβ-1b was used as a positive control.

Monocyte-Enriched Culture

To produce monocyte-enriched cultures, $2 \times 10^5$ PBMC were suspended in 100 µl of AIM-V medium and placed into each well of a 96-well plate. One hour after, floating cells were removed to leave behind adherent monocytes. Fresh 100 µl of AIM-V was added per well and cultures were kept at 37° C. Copolymer 1 was added directly to cells in the 96-well plate.

MMPs Assay

To address whether the production of MMPs by cells was affected by Copolymer 1, the conditioned medium of cells was used, since MMPs are secreted enzymes. Essentially, for floating T lymphocytes contained within the T-25 flasks, 1 ml of conditioned medium was siphoned off and microfuged for 1 min to remove cells. Supernatant was collected, mixed in a 3.1 ratio (v/v) with 4× gel-loading SDS buffer, and used in zymographic assays. Similarly, for monocytes in wells of 96-well plates, conditioned medium was collected, microfuged, and mixed with 4× gel-loading SDS buffer.

Zymography is essentially SDS-PAGE except that gelatin is also added to the gel (77, 82). After proteins were resolved based on molecular weight in SDS-PAGE, the gel was washed in a Triton X-100 buffer in order to remove SDS which thus allows protein renaturation. In a calcium-containing "reaction buffer" (77), gelatinases (MMP-2 and -9) degraded gelatin in their immediate vicinity (other members of MMPs would also be detected if present in high amounts). Following staining in Coommasie blue, which binds all proteins, and destaining , areas containing gelatinases appeared as clear bands against a dark background, since the gelatin in its immediate vicinity has been degraded. The size of the MMP bands was a reflection of the amount of MMP that was produced by cells, and this was documented by NIH image analysis software. The molecular weight of the migrated bands revealed the MMP species, which confirmed previous Western blot analyses and immunoprecipitations (77, 82).

The analysis of cell conditioned medium in zymography is a reflection of the amount of MMPs that was produced by the particular culture. To determine whether Copolymer 1 was an inhibitor of the activity of MMPs, independent from its effect on levels of MMP protein, supernatants from BHK cells, a standard source of MMPs in many laboratories, or supernatants from T lymphocytes were resolved by electrophoresis in SDS-PAGE containing gelatin. During the development of the gelatinolytic activity, Copolymer 1 was added to the Triton-100 wash, and the "reaction buffer", described above. An inhibitor of MMP activity prevents gelatin degradation by gelatinases and the resultant size of the band of gelatinases would be smaller as compared to that obtained in the absence of inhibitors.

Migration Assay

To address the migration capacity of T lymphocytes, $2 \times 10^5$ T lymphocytes in 500 µl of 2.5% fetal calf serum (FCS) containing AIM-V were seeded into the top compartment of a Boyden chamber (Collaborative Biomedical Products, Bedford, Md.). This chamber consists of two compartments separated by a polycarbonate membrane filter (9 mm in diameter, with 3 µm pores) precoated on its upper surface with fibronectin. Fibronectin was employed to simulate the basal lamina.

The bottom compartment of the migration chamber contained 10% FCS-supplemented AIM-V; the higher concentration of FCS in the bottom chamber served as a directional gradient (77). After 5 h at 37° C., the content of the lower chamber was collected, and the number of migrated T lymphocytes was counted with the Coulter Counter Z1.

Microglial Cells

Fetal human microglia were isolated from brains obtained at legal and therapeutic abortions using a protocol described by Lee et al. (41). Specimens ranged in gestational age from 14 to 20 weeks. $2.5 \times 10^4$ microglia of over 95% purity were plated per well of a 96 well plate. Microglia culture medium was minimum essential medium supplemented with 5% FCS, 0.1% dextrose. For co-cultures, 100 µl containing 50,000 T lymphocytes in AIM-V (as described above) was added to individual wells of a 96-well plate already containing 25,000 microglia (or U937 monocytoid cells—see below) in microglia culture medium. Twenty four hours after, conditioned medium was collected for cytokine quantifications by ELISA.

Adult human microglia were isolated from the resected brain tissue of patients undergoing surgical resection to treat intractable epilepsy. Microglia of over 95% purity was obtained using a previously detailed protocol (90). Cells were used for interactions with T lymphocytes in a manner identical to that described for their fetal counter parts.

A human promonocytoid cell line, U937, was also employed. Members of this cell line become microglia-like, as assessed by morphology and expression of cell surface molecules, when treated sequentially with 50 ng/ml of a protein kinase C activator, phorbol-12-myristate-13-acetate (PMA) (time 0–48) and 100 U/ml interferon-γ (IFNγ) (from 48–72 h).

Cells were used 1–3 days after the IFNγ treatment. As with microglia, 50,000 T lymphocytes in AIM-V was added to individual wells of a 96-well plate already containing 25,000 PMA/IFNγ-treated U937 cells, and conditioned medium was collected after 24 h of co-cultures.

Cytokine and Chemokine Assays

Cytokine protein levels in the conditioned medium of microglia-T lymphocyte co-cultures were measured using enzyme-linked immunoabsorbent assay (ELISA) kits bought from BioSource International (Montreal, Canada).

Chemokine and chemokine receptor expression are currently recognized to be important mechanisms that regulate the influx of leukocytes into the CNS. Notable is the up-regulation of the chemokine IP-10 and its receptor CXCR3 in the lesions of multiple sclerosis patients (74). Flow cytometry was employed to determine whether Copolymer 1 affected the expression of the CXCR3 receptor. Activated T lymphocytes or U937 cells were treated with 25 µg/ml of Copolymer 1 for 1–3 days.

RESULTS

Effect of Copolymer 1 on MMPs

Activated T lymphocytes secreted MMP-9 into the culture medium which peaked between 2–3d of anti-CD3 ligation (FIG. 1). Treatment of anti-CD3 activated T lymphocytes with Copolymer 1 (25 µg/ml, for 1, 2 or 3d) did not affect their production of MMP-9 as compared to controls (FIG. 1) and neither did a higher concentration of Copolymer 1 (50 µg/ml). Monocyte production of MMP-9 was also unaffected by Copolymer 1. In contrast, and in agreement with a previous report (77), T lymphocytes treated with IFNβ-1b produced less MMP-9 when compared to control T lymphocytes (FIG. 1).

Figure 2:
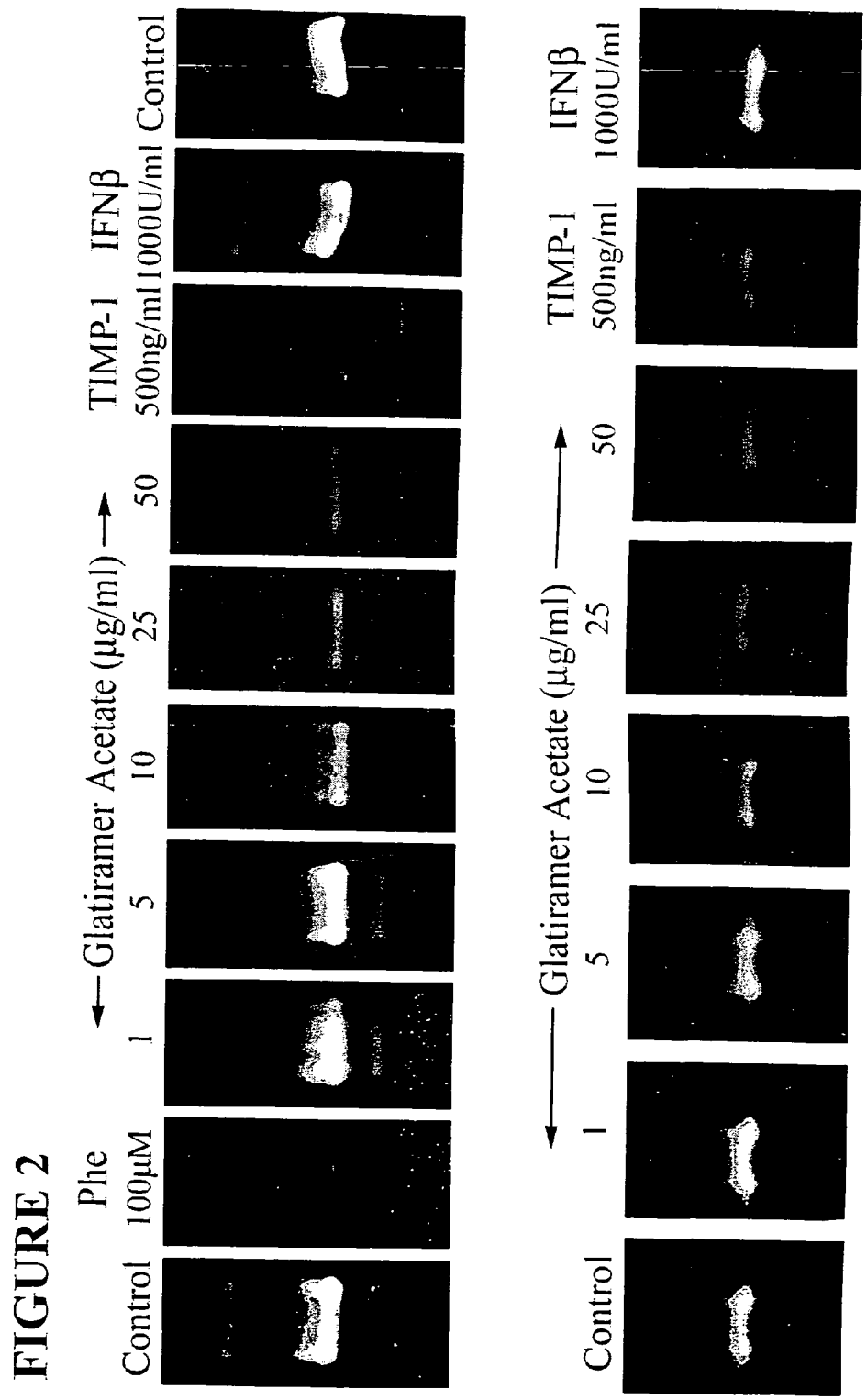
FIG. 2 demonstrates that Copolymer 1 is an inhibitor of the enzymatic activity of MMP-9. The presence of Copolymer 1 in the incubation buffers during the development of the zymograms inhibits the manifestation of MMP activity. In contrast, IFNβ-1b is not a direct MMP activity inhibitor, although it decreases the production of MMP-9 as demonstrated in FIG. 1. Positive controls, TIMP-1 and phenanthroline (phe), are shown to inhibit MMP activity in this assay.

FIG. 2 demonstrates that Copolymer 1 exhibited MMP inhibitory activity, since the size of the gelatinase band (MMP-9) was dose-dependently reduced by Copolymer 1 as compared to controls. In contrast, IFNβ-1b, which inhibits the production of MMP-9 (FIG. 1), is not a direct inhibitor of MMP enzyme activity. These results indicate that Copolymer 1 is an inhibitor of MMP enzyme activity.

Effect of Copolymer 1 on Cell Migration

Figure 3:
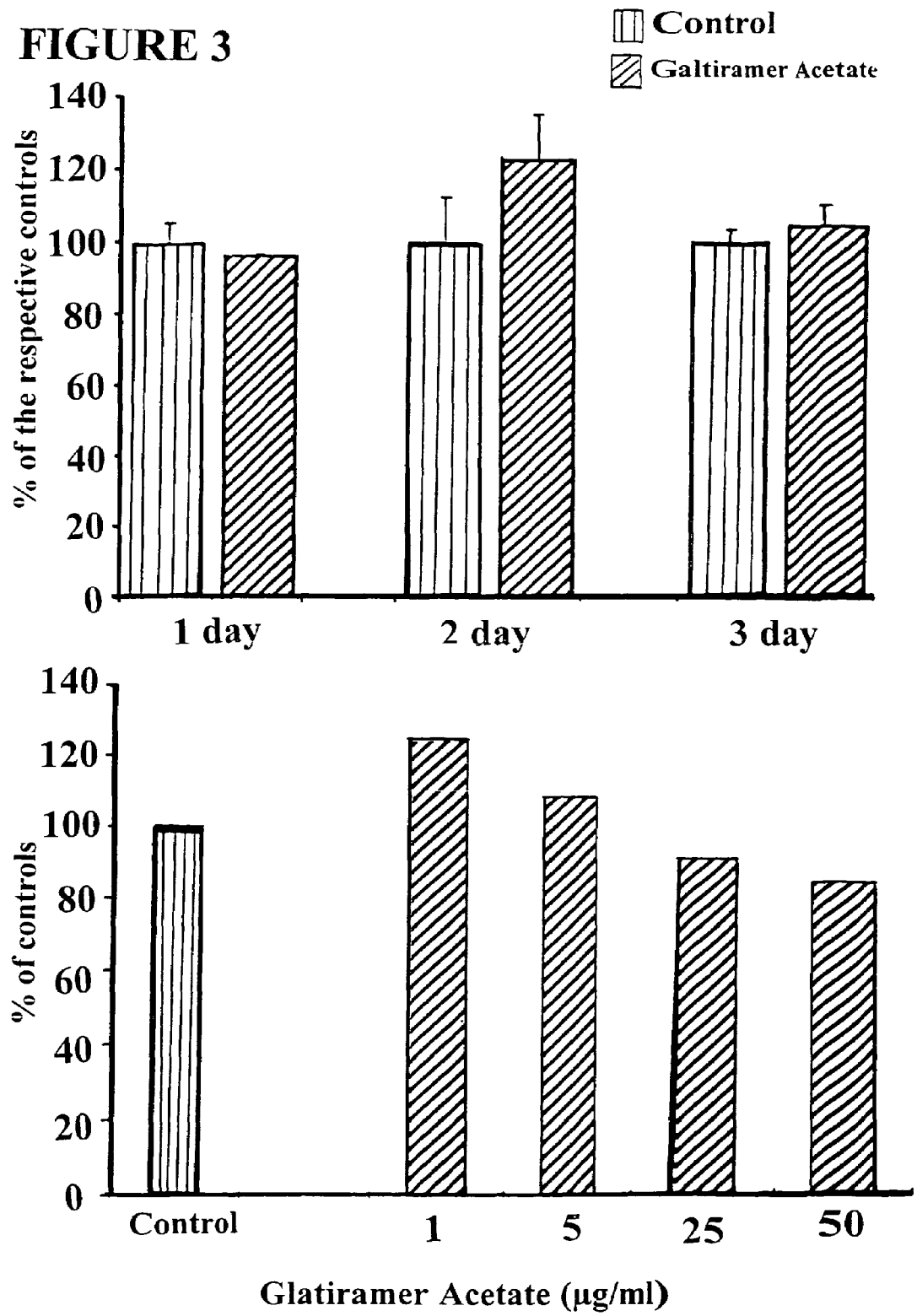
FIG. 3 reveals that Copolymer 1 does not inhibit T lymphocyte migration across a fibronectin chamber.

FIG. 3-A shows that the Copolymer 1 did not inhibit the migration of T lymphocytes when the T lymphocytes were pre-treated for 1, 2 or 3 days with Copolymer 1 (25 µg/ml). Similarly, pretreatment of T lymphocytes for 3 days with various concentrations of Copolymer 1 (1 to 50 µg/ml) did not affect the trans-migration of activated T lymphocytes (FIG. 3-B).

In a separate series of experiments, 10 ng/ml monocyte chemoattractant protein (MCP)-1 or MCP-3 was placed in the bottom chamber to serve as a chemotactic signal. Under these conditions, the migration rate of glatiramer pre-treated T lymphocytes also did not differ from that of controls.

Effect of Copolymer 1 on T Lymphocyte/Microglia Cultures

Figure 4:
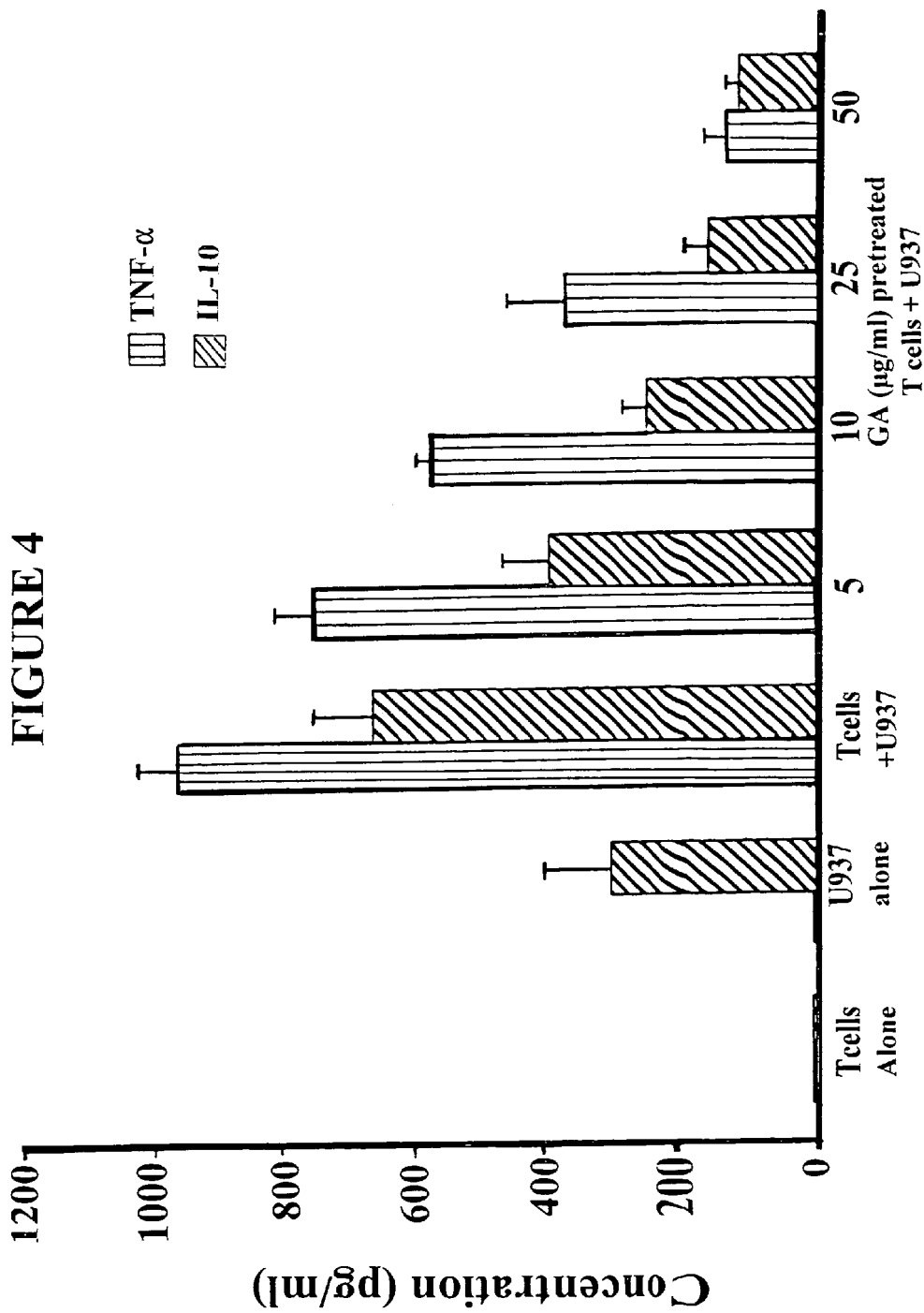
FIG. 4 shows that Copolymer 1 pretreatment of activated T lymphocytes suppresses IL-10 and TNF-α production that is generated in T lymphocyte—U937 interactions. Activated T lymphocytes in isolation produce undetectable IL-10 or TNF-α; PMA/IFNγ-pretreated U937 cells have detectable IL-10 but negligible TNF-α levels. Cytokines are significantly elevated in co-cultures and this is reduced dose-dependently by Copolymer 1 pretreatment of T lymphocytes. Values are mean±SEM of triplicate analyzes.

Neither PMA/IFNγ-treated U937 cells nor anti-CD3-activated T lymphocytes produced detectable levels of TNF-α in isolation. However, IL-10 was detected in U937 but not in T lymphocytes conditioned medium (FIG. 4). In co-culture for 24 h, substantial increases in levels of TNF-α and IL-10 were obtained. Treatment of T lymphocytes with Copolymer 1 prior to their encounter with PMA/IFNγ-treated U937 cells reduced, in a dose-dependent manner, the production of TNF-α and IL-10 (FIG. 4). The effect of Copolymer 1 appears to be principally on T lymphocytes since the pretreatment of PMA/IFNγ-treated U937 cells with Copolymer 1 did not influence cytokine production in subsequent T lymphocyte—U937 interactions.

Figure 5:
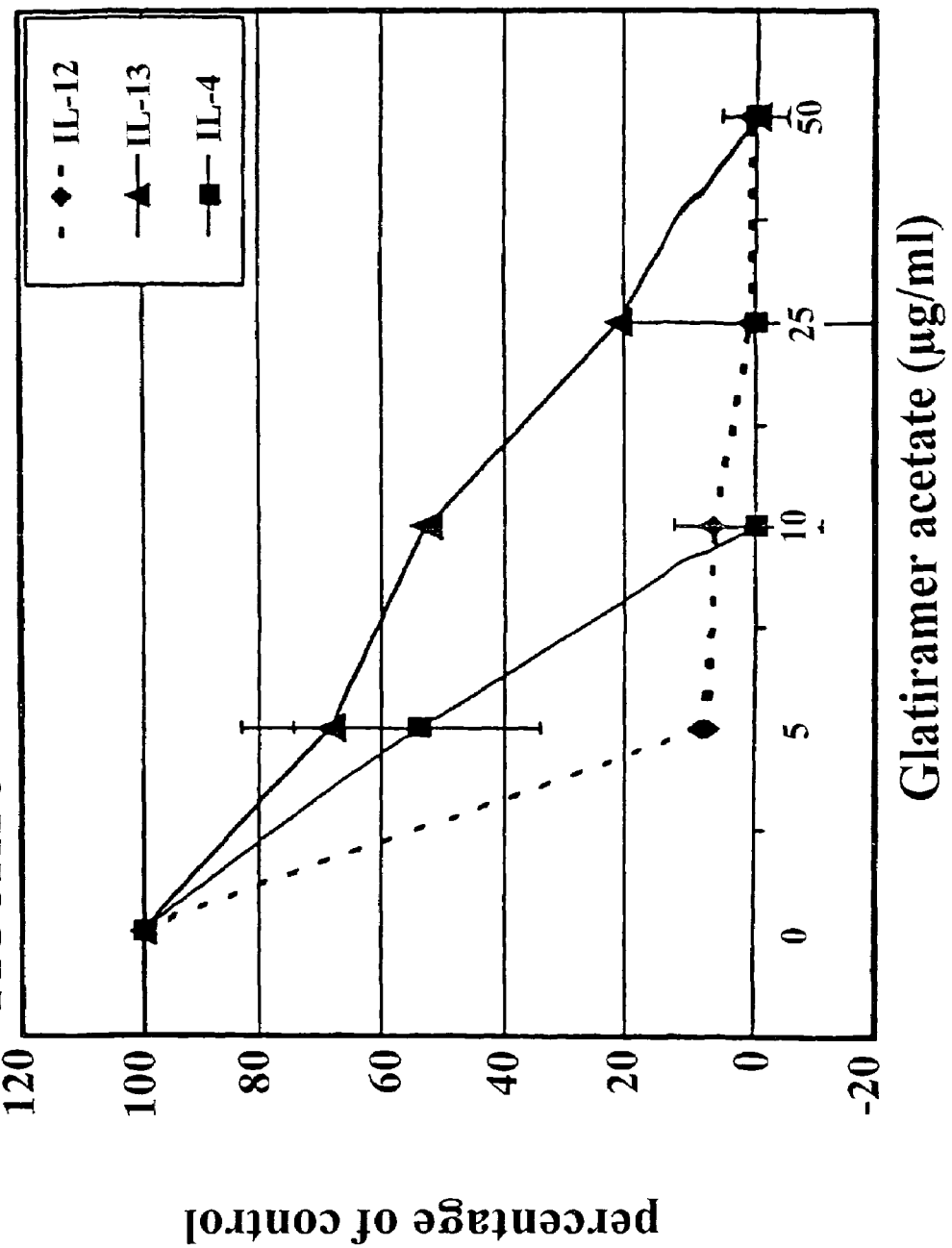
FIG. 5 reports that Copolymer 1 treatment of activated T lymphocytes also lead to the suppression of IL-4, IL-12 and IL-13 in T lymphocyte—U937 interactions. Both T lymphocytes and PMA/IFNγ-pretreated U937 cells do not secrete detectable amounts of IL-4, IL-12 or IL-13 into their conditioned medium. With co-culture, levels of these cytokines are increased, although the levels are low in comparison to those for IL-10 or TNF-α (FIG. 4); amount of IL-4, IL-12 and IL-13 in T lymphocyte—U937 interactions are, respectively, 13, 12 and 62 pg/ml. These are dose-dependently reduced by Copolymer 1 pretreatment of T lymphocytes.

Interactions between activated T lymphocyte and PMA/IFNγ-treated U937 also led to the upregulation of two Th2-like anti-inflammatory cytokines, IL-4 and IL-13 (FIG. 5), although the amounts produced were about a log fold lower than those of IL-10 or TNF-α. This production of IL-4 and IL-13 was significantly reduced by Copolymer 1 in co-cultures of T lymphocytes with PMA/IFNγ-treated U937, and this decrease was also observed for the pro-inflammatory cytokine, IL-12 (FIG. 5). In summary, Copolymer 1 pretreatment (72 h) of anti-CD3 ligated T lymphocytes results in the suppression of all inducible cytokines that were examined in the T lymphocyte-U937 interactions.

The effect of Copolymer 1 in reducing cytokine production in T lymphocyte—U937 co-cultures is not a result of a decrease in the proliferation of T lymphocytes, since Copolymer 1 does not decrease the number or size of T lymphocyte aggregates that form following anti-CD3 treatment, indicating that it does not affect the proliferation of T lymphocytes in any significant manner. Indeed, when the total number of cells was counted after 72 h of Copolymer 1, cell numbers were comparable in the control ($24\pm2\times10^3$) versus Copolymer 1-treated (5, 25 and 50 µg/ml) groups ($26\pm1$, $26\pm2$ and $22\pm1$, respectively, $\times10^3$). Equal numbers of T lymphocytes were added to microglia or U937 cells in all test situations.

Figure 6:
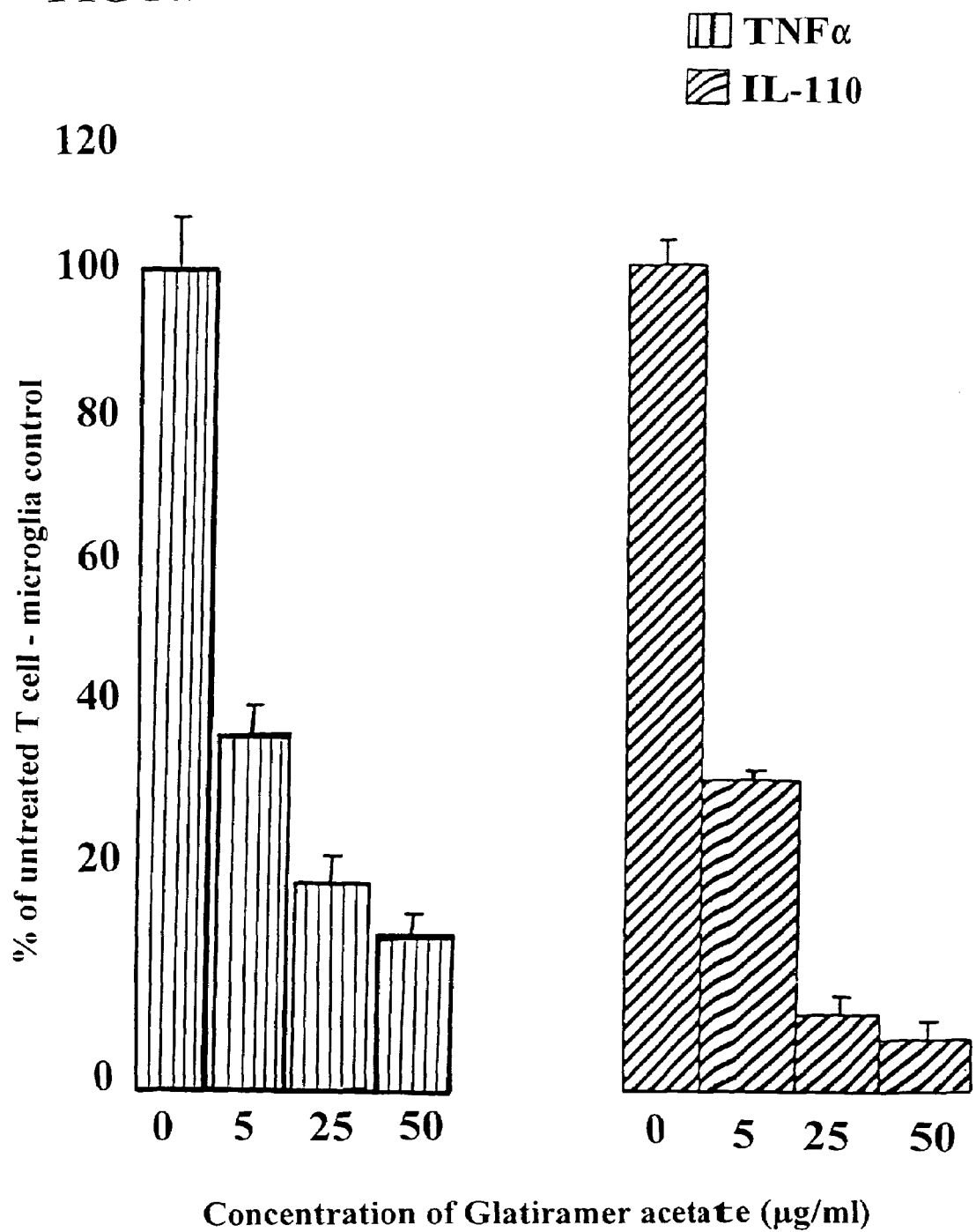
FIG. 6 demonstrates that cytokine production in co-culture of T lymphocytes with fetal human microglia is reduced by Copolymer 1. Values are mean±SEM of 3 or 4 analyzes and are expressed as % of the mean of control T lymphocyte—microglia co-cultures (i.e. 0 μg/ml Copolymer 1). The amount of TNF-α in control T lymphocyte—microglia co-culture was 1068±68 pg/ml while that for IL-10 was 139±4 μg/ml.

Fetal human microglia in isolation do not secrete detectable amounts of IL-10 or TNF-α into the culture medium; thus, it appears that these cells are similar to their adult counterparts (14, 15). In co-culture with activated T lymphocytes, significant amounts of IL-10 and TNF-α were produced ($139\pm4$ and $1068\pm68$ ng/ml, respectively, FIG. 6). With Copolymer 1 pre-treated T lymphocytes, the resultant IL-10 and TNF-α in T lymphocyte—microglia co-cultures were significantly reduced (FIG. 6). Indeed, the reduction by Copolymer 1 occurred in a dose-dependent manner (FIG. 6).

Figure 7:
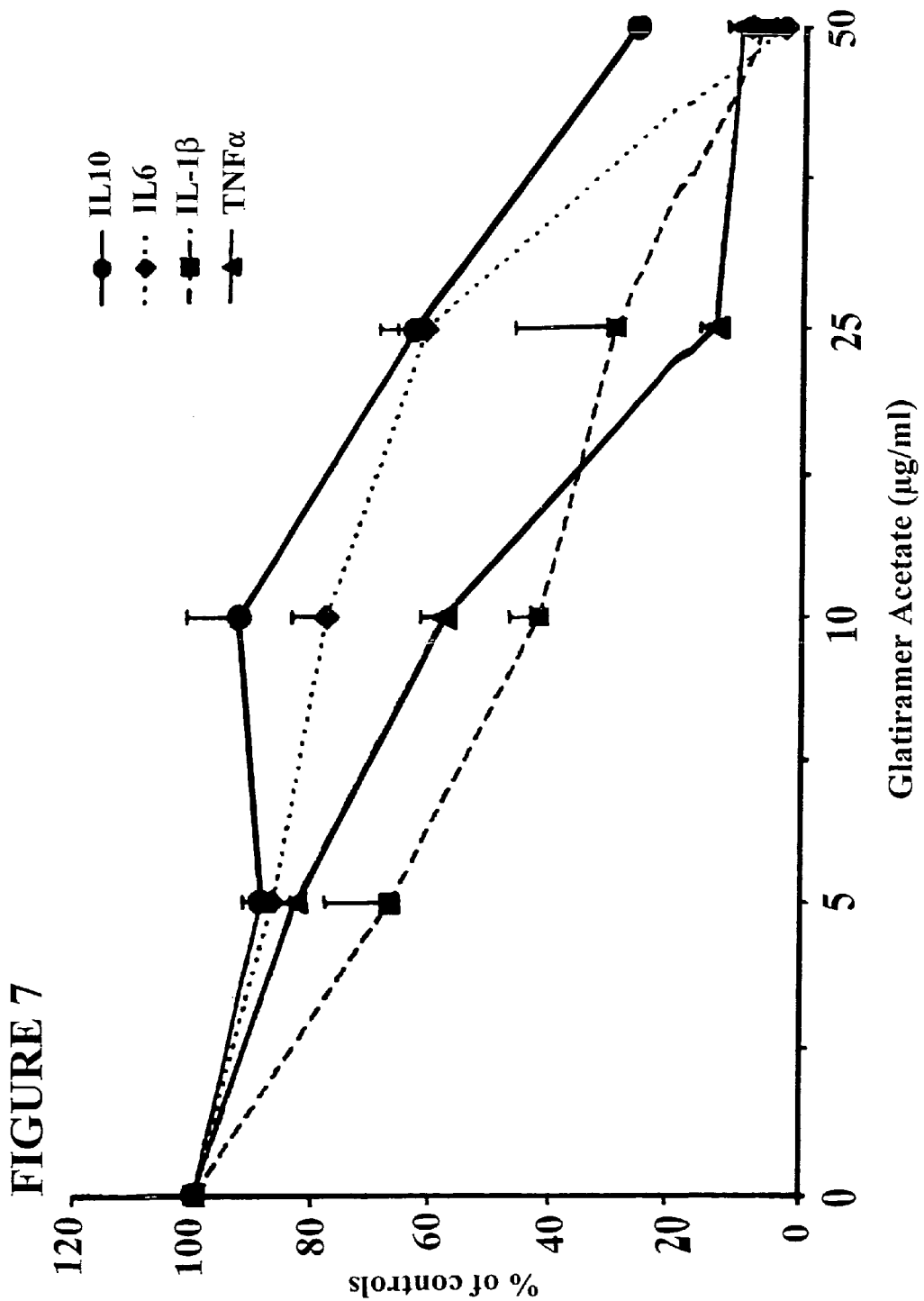
FIG. 7 reflects the effects of Copolymer 1 on cytokine production in adult human microglia and T lymphocyte co-cultures. In isolation, neither T lymphocytes nor microglia express IL-1β, IL-10 or TNF-α. In co-culture of microglia and activated T lymphocytes, the levels of cytokines induced after 24 h were 1012±86 pg/ml for TNF-α, 18±2 pg/ml for IL-1β and 46±2 pg/ml for IL-10. IL-6 is constitutively expressed in microglia (1010±215 pg/ml), but not in T lymphocytes. Copolymer 1 pretreatment of T lymphocytes reduced the level of inducible cytokines in co-culture with microglia and also the level of expression of IL-6. Values are mean+SEM of triplicate cultures.
Figure 8A:
FIG. 8 shows the morphology of microglia in T lymphocyte—microglia co-cultures.
Figure 8B:
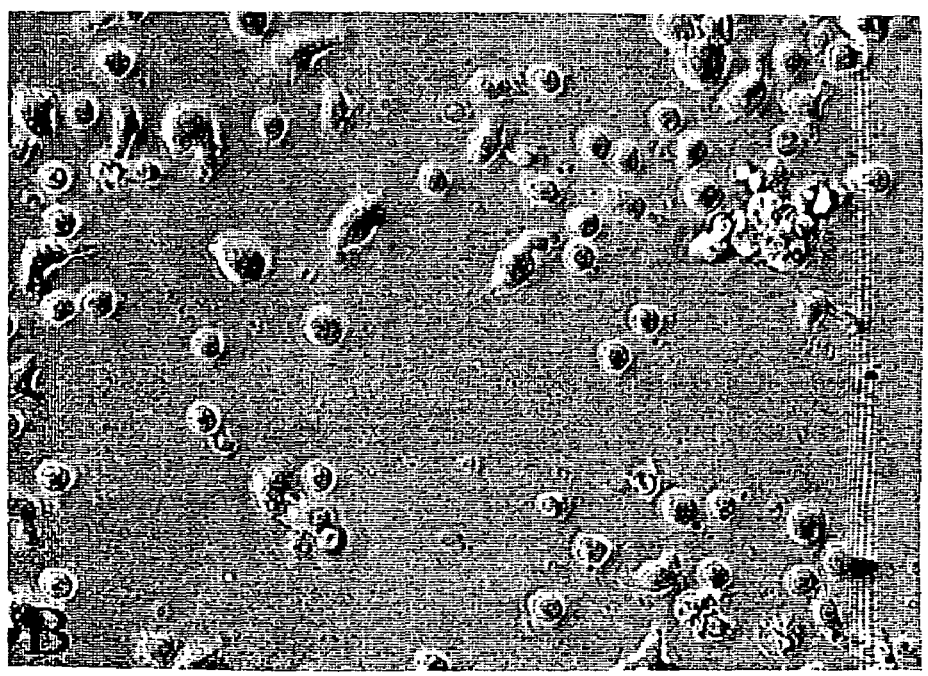
Figure 8C:
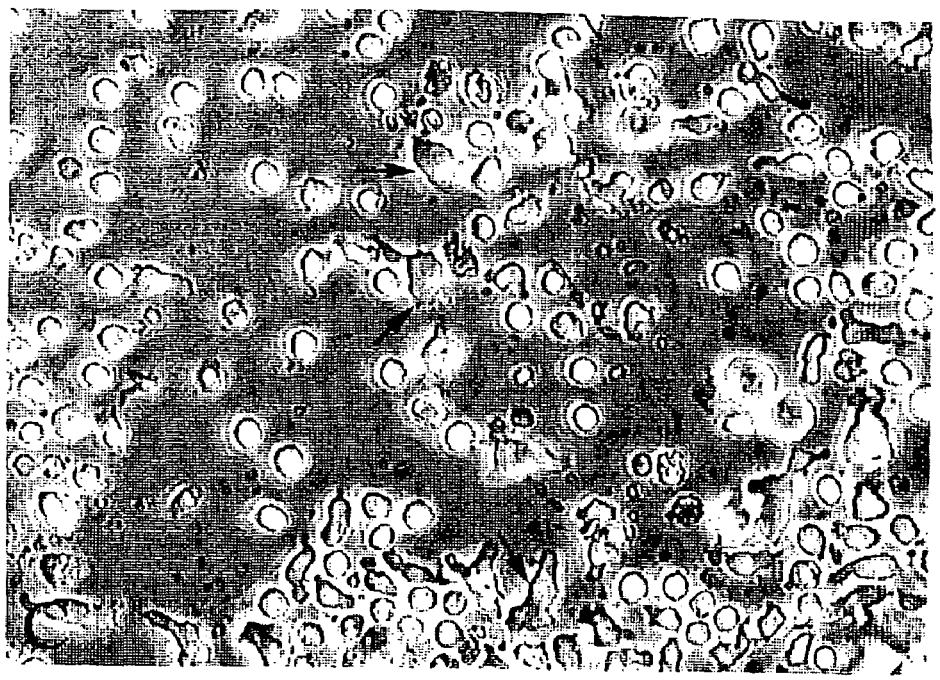
Figure 8D:
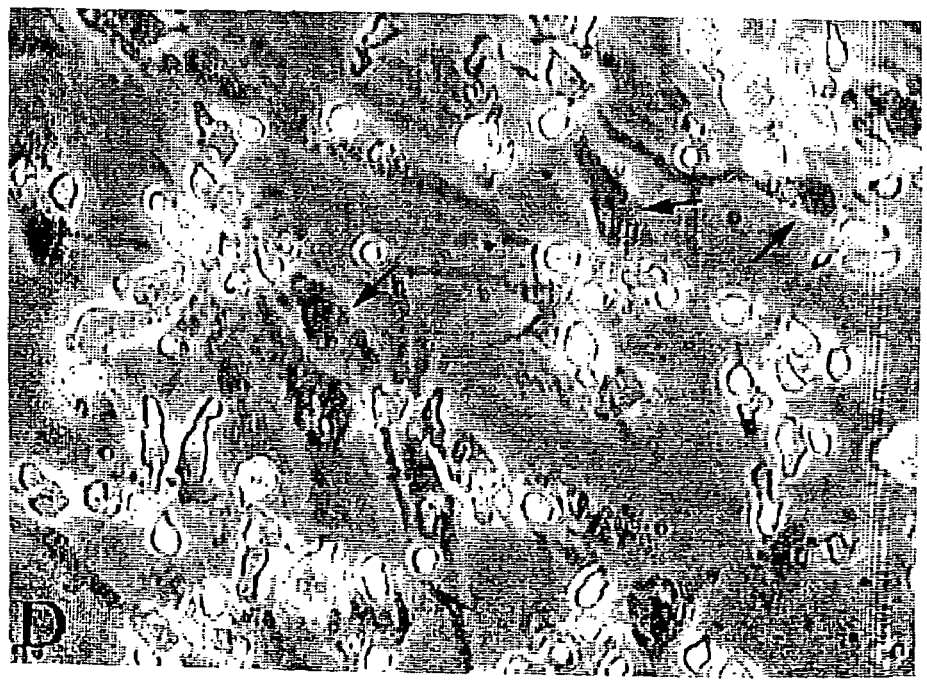

The interaction of T lymphocytes with adult microglia from human neural cells led to the upregulation of IL-10 and TNF-α from previously undetectable levels, and this was also the case for IL-1β. IL-6 was constitutively expressed at high levels by microglia (FIG. 7). The pretreatment of T lymphocytes with Copolymer 1 resulted in a dose-dependent inhibition of the inducible cytokines (IL-1, IL-10 and TNF-α). Similarly, Copolymer 1 decreased the expression of the constitutive cytokine, IL-6 (FIG. 7).

It should be noted that T lymphocytes have to be activated with anti-CD3 antibody since co-cultures of unactivated T lymphocytes (even in the presence of 50 U/ml IL-2) with microglia did not result in increased production of TNF-α. Moreover, it is necessary for T lymphocytes to be pretreated with Copolymer 1 since its reducing effect on cytokine production does not occur if it is added at the time of co-culture.

FIG. 8 demonstrates that when adult microglia encounter activated T lymphocytes in vitro, the morphology of microglia transforms from a ramified/bipolar morphology to an ameoboid rounded form (14). However, when T lymphocytes were pretreated with Copolymer 1, the morphological transformation of microglia in T lymphocyte—microglia co-culture was attenuated. This was also the case for fetal human microglia or PMA/IFNγ-treated U937 cells in co-culture with activated T lymphocytes. Overall, the lack of a morphological transformation of microglia is another indication that Copolymer 1-pretreatment of T lymphocytes resulted in their decreased ability to interact with microglia.

Effect of Copolymer 1 on Chemokines

Figure 10:
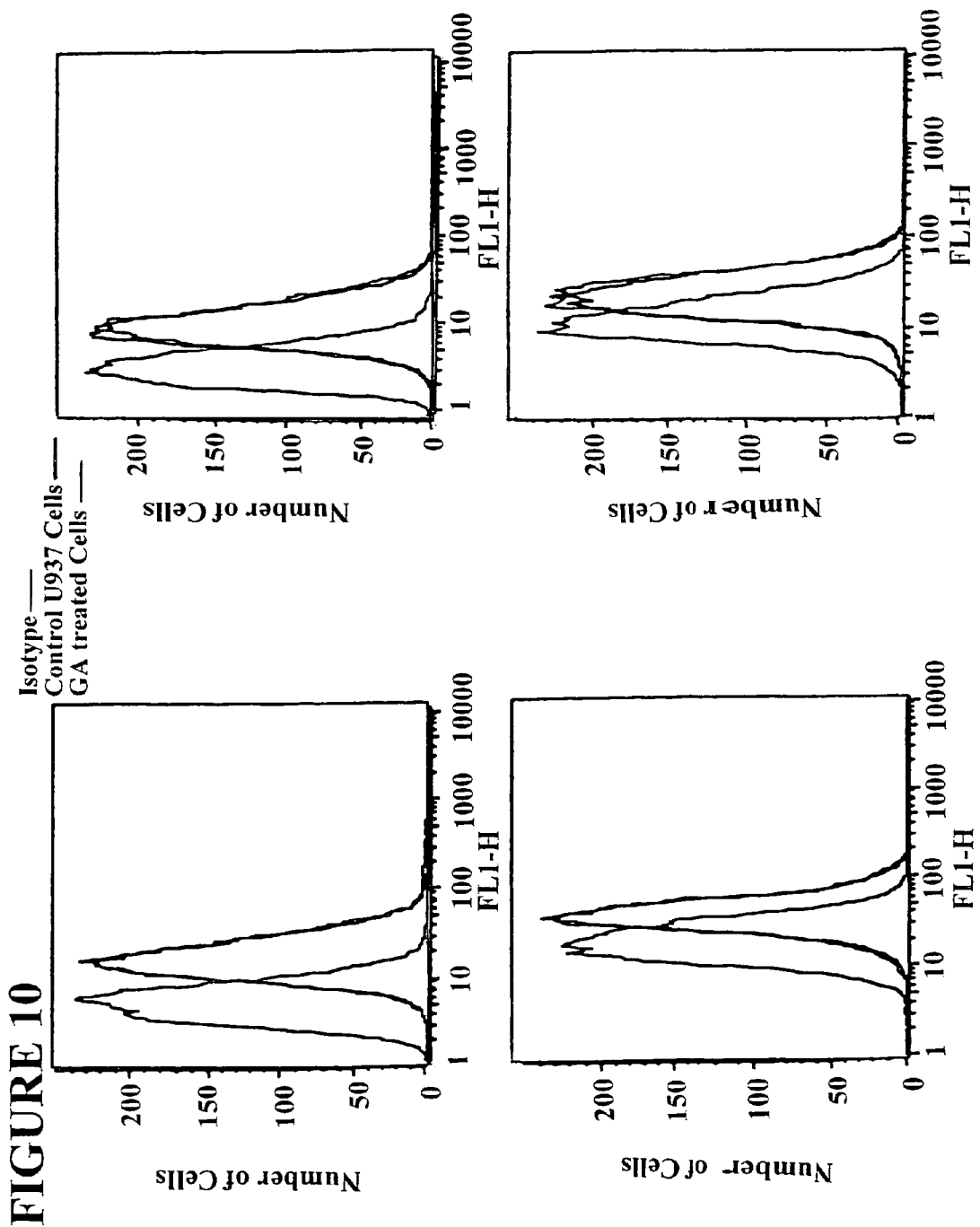
FIG. 10 demonstrates that Copolymer 1 does not affect CXCR3 and CXCR4 expression on U937 cells. Cells were treated with Copolymer 1 (25 ug/ml) or left untreated at time 0. Cells were removed and stained at 1 (FIGS. 10-A and 10-B) or 3 days (FIGS. 10-C and 10-D). An isotype control antibody was used to stain control and Copolymer 1-treated cells and the fluorsecence of these did not differ. Thus, only the isotype staining for control U937 cells is displayed.

FIG. 9 indicates that Copolymer 1 treatment of activated T lymphocytes did not reduce their expression of CXCR3 after 1–3 days of treatment; this negative result was also the case for the U937 cell line (FIG. 10). CXCR4 expression was also evaluated and found to be unresponsive to Copolymer 1 treatment.

DISCUSSION

Copolymer 1, or glatiramer acetate (GA), is a heterogeneous mixture of synthetic random linear copolymers of tyrosine, alanine, glutamic acid and lysine. This drug is effective in treating multiple sclerosis.

The mechanism of action of Copolymer 1 in multiple sclerosis is based on its capacity to suppress an immune response, which specifically affects clinical manifestations of the disease. The subject invention demonstrates that Copolymer 1 has additional biological activities, such as CNS anti-inflammation and remyelination. These findings raise the possibility of extending the potential therapeutic effect of Copolymer 1 in additional indications other than multiple sclerosis.

The capability of Copolymer 1 to bind to MHC class II molecules of various genetic backgrounds, resulting in the inhibition of T-cell responses, led to the hypothesis that it may act as a general immunosuppressor.

Results from in vivo animal models and from Copolymer 1 treated multiple sclerosis patients suggest that, in most cases, administration of Copolymer 1 in a dosing protocol that affects multiple sclerosis or EAE does not result in non-specific immunosuppression. Rather, the beneficial therapeutic effect of Copolymer 1 in multiple sclerosis and EAE is probably mediated by antigen-specific suppressor T cells.

On the other hand, administration of Copolymer 1 using different protocols (higher doses and/or more frequent administration) was shown to interfere with alloreactivity in vivo, prevent experimental GVHD and have a beneficial effect on skin and thyroid engrafment in mice models. These effects of Copolymer 1 are most probably mediated by its ability to compete with antigens for their presentation by MHC molecules on antigen presenting cells, which has been shown to be dose-dependent.

Another proof for this postulate is the fact that D-Copolymer 1—is very active in the mouse GVHD model. In fact—it is 10 times more active than L-Copolymer 1. Thus, it is reasonable to predict that using doses of Copolymer 1 higher than those used for the treatment of multiple sclerosis, will enable it to work as a general immunosuppressor, and thus to be clinically relevant in indications other than multiple sclerosis.

In view of the avid binding of Copolymer 1 to class II molecules on antigen presenting cells, studies were designed to examine whether it can interfere with T-cell mediated immune responses. Copolymer 1 reportedly inhibited in vitro T-cell responses to MBP in a dose-dependent manner (5, 11, 58, 60, 78, 80). Due to the cross-reactivity between Copolymer 1 and MBP, this effect can be attributed not only to competition for the binding to MHC class II molecules, but also to mechanisms related to T-cell recognition (1, 73). However, the inhibitory capacity of Copolymer 1 was shown to extend also to non cross-reactive T-cell responses (7, 60, 79, 83). In this case, the inhibitory effect is most probably due to competition for binding to MHC class II molecules.

Copolymer 1 binds to murine and human antigen presenting cells irrespective of their MHC restriction (promiscuous binding) in a dose-dependent manner (29, 30). Binding of Copolymer 1 to MHC class II molecules was demonstrated by its specific inhibition with anti-class II antibodies (30). Evidence for the direct interaction of Copolymer 1 with various purified HLA-DR molecules has been recently reported (28). Furthermore, Copolymer 1 was shown to compete and even displace antigens already bound to MHC class II molecules (30, 31, and 79). Binding to MHC class II molecules is rapid and efficient (30), and no processing seems to be required for this interaction (29).

A recent study observed that lymphocytes isolated from relapsing-remitting multiple sclerosis patients on Copolymer 1 were significantly reduced in their capacity to transmigrate across a fibronectin barrier, when compared to cells from untreated multiple sclerosis patients (59). Fibronectin was used as a model of basal lamina. Since the transmigration of leukocytes across the fibronectin barrier is correlated with their expression of matrix metalloproteineses (42, 77, 88), it was of interest to assess the effect of Copolymer 1 on MMPs. The subject invention shows that Copolymer 1 inhibits MMP-9 enzyme activity, but does not decrease the production of MMP-9 by T lymphocytes or monocytes. This inhibition does not alter lymphocyte transmigration.

The findings that Copolymer 1 is an inhibitor of MMP enzyme activity is relevant to MMP-mediated effects that are unrelated to leukocyte trafficking. For instance, many cytokines (e.g. TNF-α and TGF-α), cytokine receptors (e.g., TNFRs, IL-6Rα) and adhesion molecules (e.g., L-selectin, VCAM) are synthesized in pro-forms that require proteolytic processing to generate the active agent. While the identity of these "convertases" or "shedases" remains unresolved, and likely are members of another group of metalloproteinases (adamalysins), MMPs have the capacity to convert promolecules (e.g. pro-TNF-α) to their active forms (e.g. TNF-α), hence producing a proinflammatory environment within the CNS (91). The subject invention demonstrates the inhibition of MMP enzyme activity by Copolymer 1, which may decrease the conversion of procytokines to-cytokines, resulting in a non-inflammatory milieu (FIG. 2).

It has been well documented that many cells are dependent on attachment to extracellular matrix (ECM) molecules for survival. Detachment of these cells from their extracellular matrix substrate results in their apoptosis, a phenomenon that has been refered to as "anoikis" (64, 65). Because MMPs are the physiological mediators of extracellular matrix turnover, their aberrant expression and activity can disrupt the integrity of the extracellular matrix, and thus result in altered cell adhesion and death (85). By acting as an inhibitor of MMP activity, glatiramer acetate (Copolymer 1) may prevent the disruption of the extracellular matrix, and prevent the detachment of cells from the extacellular matrix. A consequence is thus decreased neural cell death and thereby the progression of the disease is slowed. MMPs are also implicated in cell-ECM interactions that govern processes as diverse as cellular differentiation, migration and inflammation. In the developing nervous system, MMP family members regulate angiogenesis, extension of neuronal growth cones and process formation by oligodendrocytes (54).

MMPs may also suppress the production of anti-inflammatory cytokines, as suggested by the findings that the treatment of EAE animals with MMP inhibitors led to the increase of the anti-inflammatory cytokine, IL-4, within the CNS (43); the mechanism of this activity remains unexplained. Other consequences of aberrant MMP expression within the CNS can include a direct role in myelin destruction (48) and the generation of encephalitogenic fragments of myelin which leads to the propagation of inflammation (16, 56). The subject finding that Copolymer 1 inhibits MMP enzyme activity could be relevant to these observations and lead to an anti-inflammatory milieu in the CNS.

The encounter of T lymphocytes with microglia is a significant source of numerous cytokines. Copolymer 1 pretreatment of T lymphocytes resulted in a substantial diminution of all cytokines tested in T lymphocyte—microglia (or U937 cell) interactions.

Immune deviation is a concept that has gained attention in recent years. This concept has its origin in the observation that uncommitted T lymphocytes can differentiate along either the Th1 route, with the production of pro-inflammatory cytokines such as IFN-$\gamma$, IL-12 or TNF-$\alpha$, or into the Th2 pathway with the production of Th2-like anti-inflammatory cytokines, including IL- 4, IL-10, IL-13 or transforming growth factor-$\beta$s (TGF-$\beta$s); cells that produce TGF-$\beta$s have also been referred to as Th3 cells. Susceptibility to certain diseases has been attributed to a predominant Th1 or Th2 response (46).

The disclosed experiments, using an antigen independent system, suggest that Copolymer 1 does not have a preferential effect on Th1 or Th2 type cytokines within the CNS, since all cytokines, including TNF-$\alpha$, IL-4, IL-6, IL-10, IL-12 and IL-13, are suppressed in the T lymphocyte—microglia interactions, creating a non-inflammatory milieu.

Although Copolymer 1 lessened the secretion of all cytokines tested (pro-inflammatory and anti-inflammatory), treatment of patients with CNS conditions should result in lessened T lymphocyte—mediated inflammation. The decreased inflammation should lessen the severity of the disease. Neuronal and axonal integrity should also improve in inflammatory CNS disorders since inflammation is also associated with the destruction of neurons and axons. Furthermore, individuals at risk for developing CNS diseases could be treated with Copolymer 1 to prevent the onset of the disease or lessen its severity. In addition, the lessened production of TNF-$\alpha$, a cytokine that is capable of killing oligodendrocytes (25, 44, 45, 69), would also decrease the degree of oligodendrocyte loss and demyelination in the CNS of patients on Copolymer 1. Additionally, Copolymer 1, by inhibition of cytokine secretion, may decrease the generation of free radicals, which cause cellular damage and destruction. Therefore, Copolymer 1 would not only alleviate the symptoms associated with CNS inflammation, but also slow the progression of the CNS disease itself.

REFERENCES

1. Aharoni, R., D. Teitelbaum, R. Arnon, M. Sela, Copolymer 1 Acts Against the Immunodominant Epitope 84–102 of Myelin Basic Protein by T-cell Receptor Antagonism in Addition to MHC Blocking, (1999), *Proc. Natl. Acad. Sci.* (USA), 96(2): 634–639.
2. Akdis, C. A., T. Blesken, M. Akdis, B. Wuthrich and K. Blaser, Role of Interleukin-10 in Specific Immunotherapy, (1998), *J. Clin. Invest.*, 102:98–106.
3. Aloisi, F., G. Penna, J. Cerase, B. Menedez Iglesias, and L. Adorini, IL-12 Production by Central Nervous System Microglia is Inhibited by Astrocytes, (1997), *J. Immunol.*, 159:1604–1612.
4. Anthony, D. C., K. M. Miller, S. Fearn, M. J. Townsend, G. Opdenakker, G. M. Wells, J. M. Clements, S. Chandler, A. J. Gearing, V. H. Perry, Matrix Metalloproteinase Expression in an Experimentally-induced DTH Model of Multiple Sclerosis in the Rat CNS, (1998), *J. Neuroimmunol.*, 87:62–72.
5. Arnon, R. and D. Teitelbaum, Desensitization of Experimental Allergic Encephalomyelitis with Synthetic Peptide Analogues, in *The Suppression of Experimental Allergic Encephalomyelitis and Multiple Sclerosis*, (1980), A. N. Davidson and M. L. Cuzner, eds., Academic Press, (New York), 105–117.
6. Balashov, K. E., J. B. Rottman, H. L. Weiner, and W. W. Hancock, CCR5+ and CXCR3+, T Cells Are Increased in Multiple Sclerosis Patients and Their Ligands MIP-1$\alpha$ and IP-10 Are Expressed in Demyelinating Lesions, (1999), *Proc. Natl. Acad. Sci.* (USA), 96:6873–6878.
7. Ben-Nun, A., I. Mendel, R. Bakimer, M. Fridkis-Hareli, et al., The Autoimmune Reactivity to Myelin Oligodendrocyte Glycoprotein (MOG) in Multiple Sclerosis Is Potentially Pathogenic: Effect of Copolymer-1 on MOG-induced Disease, (1996), *J. Neurol.*, 243:(suppl. 1):S14.
8. Berg, D. J., N. Davidson, R. Kuhn, W. Muller, S. Menon, G. Holland, L. Thompson-Snipes, M. W. Leach, and D. Rennick, Enterocolitis and Colon Cancer in Interleukin-10-deficient Mice are Associated with Aberrant Cytokine Production and CD4$^+$ Th1-like Responses, (1996), *J. Clin. Invest.*, 98:1010-1020.
9. Bogdan, C., Y. Vodovotz, and C. Nathan, Macrophage Deactivation by Interleukin-10, (1991), *J. Exp. Med.*, 174:1549–1555.
10. Brandtzaeg, P., L. Osnes, R. Ovstebo, G. B. Joo, A. B. Westvik, and P. Kierulf, Net Inflammatory Capacity of Human Septic Shock Plasma Evaluated by a Monocyte-based Target Cell Assay: Identification of Interleukin-10 as a Major Functional Deactivator of Human Monocytes, (1996), *J. Exp. Med.*, 184:51–60
11. Burns, J. and K. Littlefield, Failure of Copolymer I to Inhibit the Human T-cell Response to Myelin Basic Protein, (1991), *Neurology*, 41:1317–1319.
12. Butt, A. M., and H. G. Jenkins, Morphological Changes in Oligodendrocytes in the Intact Mouse Optic Nerve Following Intravitreal Injection of Tumor Necrosis Factor, (1994), *J. Neuroimmunol.*, 51:27–33.
13. Canella, B., and C. S. Raine, The Adhesion Molecule and Cytokine Profile of Multiple Sclerosis Lesions, (1995), *Ann. Neurol.*, 37:424–435.
14. Chabot, S., G. Williams, M. Hamilton, G. Sutherland, and V. W. Yong, Mechanisms of IL-10 Production in Human Microglia—T Cell Interaction, (1999), *J. Immunol.*, 162:6819–6828.
15. Chabot, S., G. Williams, and V. W. Yong, Microglial Production of TNF-$\alpha$ in Induced by Activated T Lymphocytes: Involvement of VLA-4 and Inhibition by Interferonβ-1b, (1997), *J. Clin. Invest.*, 100:604–612.

16. Chandler, S., K. M. Miller, J. M. Clements, J. Lury, D. Corkill, D. C. C. Anthony, S. E. Adams, and A. J. H. Gearing, Matrix Metalloproteinases, Tumor Necrosis Factor and Multiple Sclerosis: An Overview, (1997), *J. Neuroimmunol.*, 72:155–161.

17. Compston, D. A. S., "Genetic Susceptibility to Multiple Sclerosis," in *McAlpine's Mutiple Sclerosis*, (1991), Matthews, B. ed., Churchil Livingstone, (London), 301–319.

18. Cossins et al., Enhanced Expression of MMP-7 and MMP-9 in Demyelinating Multiple Sclerosis Lesions, (1997), *Acta Neuropathol. (Berl.)*, 94(6):590–8.

19. Cross, A. H., B. Canella, C. F. Brosnan, and C. S. Raine, Homing to Central Nervous System Vasculature by Antigen-specific Lymphocytes. I. Localization of 14C-labeled Cells During Acute, Chronic and Relapsing Experimental Allergic Ecephalomyelitis, (1993), *Lab. Invest.*, 63:253–258.

20. Cross, A. H., T. O'Mara, and C. S. Raine, Chronologic Localization of Myelin-reactive Cells in the Lesions of Relapsing EAE, *Neurology*, (1993), 43:1028–1033.

21. Cuzner et al., The Expression of Tissue-type Plasminogen Activator, Matrix Metalloproteases and Endogenous Inhibitors in the Central Nervous System in Multiple Sclerosis: Comparison of Stages in Lesion Evolution, (1996), *J. Neuro. Pathol. Exp. Neurol.*, 55(12):1194–204

22. Darnell et al., *Molecular Cell Biology*, $2^{nd}$ ed., New York: Scientific American Books, (1990), 768, 778–79, 1038, 1040.

23. Davidson, N. J., M. W. Leach, M. M. Fort, L. Thompson-Snipes, R. Kuhn, W. Muller, D. J. Berg, and D. M. Rennick, T Helper Cell I-type $CD4^+$ T Cells, but not B Cells, Mediate Colitis in Interleukin-10-deficient Mice, (1996), *J. Exp. Med.*, 184:241–251.

24. De Waal Malefyt, R., J. Abrams, B. Bennett, C. G. Fogdor, and J. E. de Vries, Interleukin-10 (IL-10) Inhibits Cytokine Synthesis by Human Monocytes: an Autoregulatory Role of IL-10 Produced by Monocytes, (1991), *J. Exp. Med.*, 174:1209–1220.

25. D'Souza, S., K. A. Alinauskas, and J. P. Antel, Ciliary Neurotrophic Factor Selectively Protects Human oligodendrocytes from Tumor Necrosis Factor-mediated Injury, (1996), *J. Neurosci. Res.*, 43:289–298.

26. D'Souza, S., K. Alinauskas, E. Macrea, C. Goodyer, and J. P. Antel, Differential Susceptibility of Human CNS-derived Cell Populations to TNF-dependent and Independent-immune-Mediated Injury, (1995), *J. Neurosci.*, 15:7293–7300.

27. Endo et al., LPS-dependent Cyclooxygenase-2 Induction in Human Monocytes is Down-regulated by IL-13, but not by IFN-Gamma (1996), *J. Immunol.*, 156:2240–6.

28. Fridkis-Hareli, M., and J. L. Strominger, Promiscuous Binding of Synthetic Copolymer 1 to Purified HLA-DR Molecules, (1998), *J. Immunol.*, 160:4386–4397.

29. Fridkis-Hareli, M., D. Teitelbaum, R. Arnon, M. Sela, Synthetic Copolymer-1 and Myelin Basic Protein do not Require Processing Prior to Binding to Class II Major Histcompatibility Complex Molecules on Living Antigen Presenting Cells, (1995), *Cell. Immunol.*, 163:229–236.

30. Fridkis-Hareli, M., D. Teitelbaum, E. Gurevich, I. Pecht, et al., Direct Binding of Myelin Basic Protein and Synthetic Copolymer-1 to Class II Major Histocompatability Complex Molecules on Living Antigen. Presenting Cells—Specificity and Promiscuity, (1994), *Proc. Natl. Acad. Sci.* (USA), 91:4872–4876.

31. Fridkis-Hareli, M., D. Teitelbaum, D. E. Kerlero, R. Rosbon, Arnon, et al., Synthetic Copolymer-1 Inhibits the Binding of MBP, PLP and MOG Peptides to Class II Major Histocompatibility Complex Molecules on Antigen Presenting Cells, (1994), *J. Neurochem.*, 63(suppl. 1):S61D (Abstract).

32. Gijbels, K., R. E. Galardy, and L. Steinman, Reversal of Experimental Autoimmune Encephalomyelits with a Hydroxamate Inhibitor of Matrix Matalloproteases, (1994), *J. Clin. Invest.* 94:2177–2182.

33. Hafler, D. A. and Weiner, H. L., MS: A CNS and Systemic Autoimmune Disease, (1989), *Immunol. Today*, 10:104–107.

34. Hewson, A. K., T. Smith, J. P. Leonard, and M. L. Cuzner, Suppression of Experimental Allergic Encephalomyelits in the Lewis Rat by the Matrix Metalloproteinases Inhibitor RO31–9790, (1995), *Inflam. Res.*, 44:345349.

35. Hofman, F. M., D. R. Hinton, K. Johnson, and J. E. Merrill, Tumor Necrosis Factor Identified in Multiple Sclerosis Brain, (1989), *J. Exp. Med.*, 170:607–612.

36. Iglesias, B., J. Cerase, C. Ceracchini, G. Levi, and F. Aloisi, Analysis of B7-1 and B7-2 Costimulatory Ligands in Cultured Mouse Microglia: Upregulation by Interferon γ and Lipopolysaccharide and Downregulation by Interleukin-10, Prostaglandin E2 and Cyclic AMP-elevating Agents, (1997), *J. Neuroimmunol.*, 72:83–93.

37. Keiseier, B. C., T. Seifert, G. Giovannoni, and H. P. Hartung, Matrix Metalloproteinases in Inflammatory Demyelination, Targets for Treatment, (1999), *Neurol.*, 53:20–25.

38. Koch, F., U. Stanzl, P. Jennewein, K. Janke, C. Heufler, E. Kampgen, N. Romani, and G. Schuler, High Levels of IL-12 Production by Marine Dendritic Cells: Upregulation via MHC Class II and CD4 Molecules and Down-regulation by IL-4 and IL-10, (1996), *J. Exp. Med.*, 184:741–746

39. Kuhn, R., J. Lohler, D. Rennick, K. Rajewsky, and W. Muller, Interleukin-10-deficient Mice Develop Chronic Enterocolitis, (1993), *Cell*, 75:263–274.

40. Lee, M. A., J. Palace, G. Stabler, J. Ford, A. Gearing, and K. Miller, Serum Gelatinase B, TIMP-1 and TIMP-2 Levels in Multiple Sclerosis, A Longitudinal Clinical and MRI Study, (1999), *Brain*, 122:191–197.

41. Lee, S. C., W. Liu, C. F. Brosnan, and D. W. Dickson, Characterization of Primary Human Fetal Dissociated Central Nervous System Cultures with an Emphasis on Microglia, (1992), *Lab. Invest.*, 67:465–476.

42. Leppert, D., E. Waubant, R. Galardy, N. W. Bunnett, and S. L. Hauser, T Cell Gelatinases Mediate Basal Membrane Transmigration in Vitro, (1995), *Immunol.*, 154:4379–4389.

43. Liedtke, W., B. Cannella, R. J. Mazzaccaro, J. M. Clements, K. M. Miller, K. W. Wucherpfennig, A. J. Gearing, and C. S. Raine, Effective Treatment of Models of Multiple Sclerosis by Matrix Metalloproteinases Inhibitors, (1998), *Ann. Neurol.*, 44:35–46.

44. Loughlin, A. J., P. Honnegar, M. N. Woodroofe, V. Comte, J. M. Matthieu, and M. L. Cuzner, Myelin Basic Protein Content of Aggregating Rat Brain Cell Cultures Treated with Cytokines and/or Demyelinating Antibody: Effects of Macrophage Enrichment, (1994), *J. Neurosci. Res.*, 37:647–653, 45. Louis J. C., E. Magal, S. Takayama, and S. Varon, CNTF Protection of Oligodendrocytes Against Natural and Tumor Necrosis Factor α-induced Death, (1993), *Science*, 259:689–692.

46. Lucey, D. R., Evolution of the Type-1 (Th1)-type-2 (Th2) Cytokine Paradigm, (1999), *Infect. Dis. Clin.*, 13(1): 1–9.
47. Maeda and Sobel, Matrix Metalloproteinases in the Normal Human Central Nervous System, Microglia Nodules, and Multiple Sclerosis Lesions, (1996) *J. Neuropathol. Exp. Neurol.*, 55(3):300–309.
48. Matyszak, M. K. and V. H Perry, Inflammation Induced Breakdown of the BBB and Demyelination are Prevented by Inhibitors of Matrix Metalloproteinases, (1996), *J. Neuroimmunol.*, 69:141–149.
49. Mizuno, T., M. Sawada, T. Marunoouchi, and A. Suzumura, Production of Interleukin-10 by Mouse Glial Cells in Culture, (1994), *Biochem. Biophys. Res. Commun.*, 205:1907–1915.
50. Nagase, H., Activation Mechanisms of Matrix Metalloproteineses, (1997), *Biol. Chem.*, 378:151–160.
51. Nassar et al., Induction of 15-Lipoxygenase by Interleukin-13 in Human Blood Monocytes, (1994), *J. Biol. Chem.*, 269(44):27631–4.
52. Norga, K., L. Paemen, S. Masure, C. Dillen, H. Heremans, A. Billiau, H. Carton, L. Cuzner, T. Olsson, J. Van Damme, and G. Opdenakker, Prevention of Acute Autoimmune Encephalomyelits and Abrogation of Relapses in Murine Models of Multiple Sclerosis by the Protease Inhibitor D-penicillamine, (1995), *Inflam. Res.*, 44:529–534.
53. Noseworthy, J. H., Progress in Determining the Causes and Treatment of Multiple Sclerosis, (1999), *Nature*, 399:A40–47.
54. Oh, L. Y. S., C. Krekoski, F. Donovan, D. Edwards, Z. Werb, V. W. Yong, Gelatinase B/Matrix Metalloproteinases-9 is Required for Oligodendroglial Process Extension in Vivo and in Vitro, (1999), *J. Neurosci.*, 19:8464–8475.
55. Olsson, T., Immunology of Multiple Sclerosis, (1992), *Curr. Opin. Neurol. Neurosurg.*, 5:195–202.
56. Opdenakker, G. and J. Van Damme, Cytokine-regulated Proteases in Autoimmune Disease, (1994), *Immunol. Today*, 15:103–107.
57. Ozenci et al., Metalloproteinases and their Tissue Inhibitors in Multiple Sclerosis, (1999), *J. Autoimmun.*, 12(4): 297–303.
58. Parkman, R., Graft-versus-host Disease, (1991), *Ann. Rev. Med.*, 42: 189–197.
59. Prat, A., A. Al-Asmi, P. Duquette, and J. P. Antel, Lymphocyte Migration and Multiple Sclerosis: Relation with Disease Course and Therapy, (1999), *Ann. Neurol.*, 46:253–256.
60. Racke, M. K., R. Martin, H. McFarland, R. B. Fritz, Copolymer-1 Induced Inhibition of Antigen-specific T-cell Activation: Interference with Antigen Presentation, (1992), *J. Neuroimmunol.*, 37:75–84.
61. Raivich, G., L. L. Jones, C. U. A. Kloss, A. Werner, H. Neumann, and G. W. Kreutzberg, Immune Surveillance in the Injured Nervous System: T-lyphocytes Invade the Axotomised Mouse Facial Motor Nucleus and Aggregate Around Sites of Neuronal Degeneration, (1998), *J. Neurosci.*, 18:5804–5818.
62. Reickman, N. P., M. Albrecht, B. Kitze, T. Weber, H. Tumani, A. Broocks, W. Luer, A. Helwig, and S. Poser, Tumor Necrosis Factor-α Messenger RNA Expression in Patients with Relapsing-remitting Multiple Sclerosis is Associated with Disease Activity, (1995), *Ann. Neurol.*, 37:82–88.
63. Ruddle, N. H., C. Bergman, K. McGrath, E. Lingenheld, M. Grunnet, S. Padula, and R. Clark. An Antibody to Lymphotoxin Prevents Transfer of Experimental Allergic Encephalomyelitis, (1990), *J. Exp. Med.*, 172:193–1200.
64. Ruoslahti, E., and J. C. Reed, Anchorage Dependence, Intergrins and Apoptosis, (1994), *Cell*, 77:477–478.
65. Ruoslahti, E., and A. Valerie, Cell-to-cell Contact and Extracellular Matrix, (1997), *Curr. Opin. Cell. Biol.*, 9:605–607.
66. Schrijver, H. M., J. B. A. Crusius, B. M. J. Uitehaag, G. Gonzalez, P. J. Kostense, C. H. Polman, and A. S. Pena, Association of Interleukin-1β and Interleukin-1 Receptor Antagonist Genes with Disease Severity in MS, (1999), *Ann. Neurol.*, 52:595–599.
67. Sedgwick, J., S. Brostoff, and D. Mason, Experimental Allergic Encephalomyelits in the Absence of a Classical Delayed-type Hypersensitivity Reaction: Severe Paralytic Disease Correlates with the Presence of Interleukin-2 Receptor-positive Cells Infiltrating the Central Nervous System, (1987), *J. Exp. Med.*, 165:1058–1075.
68. Sedgwick, J. D., A. L. Ford, E. Foulcher, and R. Airriess, Central Nervous System Microglial Cell Activation and Proliferation Follows Direct Interaction with Tissue-infiltrating T Cell Blasts, (1998), *J. Immunol.*, 160:5320–5330.
69. Selmaj, K. W., Papeirz, A. Glabinski, and T. Rohno, Prevention of Chronic Relapsing Experimental Autoimmune Encephalomyelitis by Soluble TNF Receptor 1, (1995), *J. Neuroimmunal.*, 56:135–141.
70. Selmaj, K. W., Paperirz, and C. S. Raine, Experimental Autoimmune Excephalomyelitis Immunotherapy with Anti-tumor Necrosis Factor Antibodies and Soluble Tumor Necrosis Factor Receptors, (1995), *Neurology*, 45:S44–S49.
71. Selmaj, K. W. and C. S. Raine, Tumor Necrosis Factor Mediates Myelin and Oligodendrocyte Damage in Vitro, (1988), *Ann. Neurol.*, 23:339–346.
72. Selmaj, K. W., C. S. Raine, B. Cannella, and C. F. Brosnan, Identification of Lymphotoxin and Tumor Necrosis Factor in Multiple Sclerosis Lesions, (1991), *J. Clin. Invest.*, 87:949–954.
73. Shulman, H. M., Sullivan K. M., Weiden P. L., et al., Chronic Graft-versus-Host Disease in Man. A Long Term Clinical Pathological Study of 20 Seattle Patients, (1980), *Am. J. Med.*, 69:204–217.
74. Sorensen, T. L., M. Tani, J. Jensne, V. Pierce, C. Lucchinetti, V. A. Folcik, S. Qin, J. Rottman, F. Sellebjerg, R. M. Streiter, J. L. Frederiksen, and R. M. Ransohoff, Expression of Specific Chemokines and Chemokine Receptors in the Central Nervous System of Multiple Sclerosis Patients, (1999), *J. Clin. Invest.*, 103: 807–815.
75. Sornasse et al., Differentiation and Stability of T Helper 1 and 2 Cells Derived From Naive Human Neonatal CD4+ T Cells, Analyzed at the Single-cell Level (1996), *J. Exp. Med.*, 184:473–83.
76. Springer, T. A., Adhesion Receptors of the Immune System, (1990), *Nature (Lond.)*, 346:425–434.
77. Stuve, O., N. P. Dooley, J. H. Uhm, J. P. Antel, G. Williams, and V. W. Yong, Interferon-β Decreases the Migration of T Lymphocytes in Vitro: Effects on Matrix Metalloproteinases-9, (1996), *Ann. Neurol.*, 40:853–863.
78. Teitelbaum, D., R. Aharoni, R. Arnon, M. Sela, Specific Inhibition of the T-cell Response to Myelin Basic Protein by the Synthetic Copolymer COP-1, (1988), *Proc. Natl. Acad. Sci.* (USA), 85:9724–9728.
79. Teitelbaum, D., M. Fridkis-Hareli, R. Arnon, M. Sela, Copolymer-1 Inhibits Chronic-relapsing Experimental Allergic Encephalomyelitis Induced by Proteolipid Pro- 80. Teitelbaum, D., R. Milo, R. Arnon, M. Sela, Synthetic Copolymer 1 Inhibits Human T-cell Lines Specific for Myelin Basic Protein, (1992), *Pro. Natl. Acad. Sci.* (USA), 89:137–141.
81. Thompson et al., Chemotactic and Suppressor Cytokine Networks, (1996), *Hepatogastroenterology,* 43(7):15–31.
82. Uhm, J. H., N. P. Dooley, L. Y. Oh, V. W. Yong, Oligodendrocytes Utilize a Matrix Metalloproteinase, MMP-9, to Extend Processe along an Astrocyte Extracellular Matrix, (1998), *Glia,* 22:53–63.
83. Van Sehel, A. C. and J. M. Van Noort, Copolymer-1 Inhibits Human T-cell Responses to the Major Myelin Antigen Alpha B-crystallin, (1996), *J. Neurol.,* 243: (suppl. 2):S40 (Abstract).
84. Waubant, E., D. E. Goodkin, L. Gee, P. Bacchetti, R. Sloan, T. Stewart, P. B. Anderson, G. Stabler, and K. Miller, Serum MMP-9 and TIMP-1 Levels Are Related to MRI Activity in Relapsing Multiple Sclerosis, (1999), *Neurol.,* 53:1397–1401.
85. Werb, Z., and E. C. M. Cell Surface Proteolysis: Regulating Cellular Ecology, (1997) *Cell,* 91:439–442.
86. Williams, K., N. Dooley, E. Ulvestad, B. Becher, and J. P. Antel, IL-10 Production by Adult Human Derived Microglial Cells, (1996), *Neurochem. Int.,* 29:55–64.
87. Wong et al., Interleukin (IL) 1beta, IL-1 Receptor Antagonist, IL-10, and IL-13 Gene Expression in the Central Nervous System and Anterior Pituitary During Systemic Inflammation: Pathophysiological Implications, (1997), *Proc. Natl. Acad. Sci.* (USA), 94:227–32.
88. Xia, M., D. Leppert, S. L. Hauser, S. P. Sreedharan, P. J. Nelson, A. M. Krensky, E. J. Goetzl, Stimulus Specificity of Matrix Metalloproteinases Dependence of Human T Cell Migration Through a Model Basal Membrane, (1996), *J. Immunol.,* 156:160–167.
89. Yong, V. W., The Potential Use of MMP Inhibitors to Treat CNS Diseases, (1999), *Expert Opinion on Investigational Drugs,* 8:255–268.
90. Yong, V. W., and J. P. Antel, Culture of Glial Cells from Human Brain Biopsies, *Protocols for Neural Cell Culture,* 2$^{nd}$ Edition, (1997), A. Richardson and S. Fedoroff, eds., Humana Press, (St. Louis), 157–172.
91. Yong, V. W., C. A. Krekoski, P. A. Forsyth, R. Bell, and D. R. Edwards, Matrix Metalloproteinases and Diseases of the Central Nervous System, (1998), *Trends Neurosci.,* 21:75–80.
92. "Copaxone®", *Physician's Desk Reference,* (2000), Medical Economics Co., Inc., (Montvale, N.J.), 3115.

What is claimed is:

1. A method of alleviating inflammatory symptoms of a disease in a mammalian subject suffering from an inflammatory non-autoiminune disease, wherein the disease is a brain tumor, or a central nervous system viral infection or a central nervous system bacterial infection, which comprises administering glatiramer acetate to the subject in an amount and for a duration of time effective to inhibit matrix metalloproteinase and reduce the generation of free radicals which cause cellular damage so as to alleviate the inflammatory symptoms of the disease in the subject.

2. The method of claim 1, wherein the mammalian subject is a human.

3. The method of claim 1, wherein the disease is a brain tumor.

4. The method of claim 1, wherein the disease is a central nervous system viral infection or a central nervous system bacterial infection.

5. The method of claim 4, wherein the disease is a central nervous system viral infection.

6. The method of claim 5, wherein the central nervous system viral infection is HIV encephalopathy.

7. The method of claim 4, wherein the disease is a central nervous system bacterial infection.

8. The method of claim 7, wherein the bacterial infection is meningitis.

9. The method of claim 1, wherein the amount of glatiramer acetate administered ranges from about 0.05 mg/kg of body weight to about 50 mg/kg of body weight.

10. The method of claim 1, wherein the amount of glatiramer acetate administered ranges from about 0.1 mg to about 1000 mg.

11. The method of claim 1, wherein the glatiramer acetate is administered by an oral, intravenous, intramuscular, subcutaneous, intraperitoneal, transdermal, nasal or rectal route.

12. The method of claim 11, wherein the route of administration is oral administration.

13. The method of claim 11, wherein the route of administration is subcutaneous injection.

14. The method of claim 1, wherein the axnount of glatiramer acetate is administered at a frequency of about once every 30 days to about once every day.

15. The method of claim 1, wherein the glatiramer acetate administration decreases the conversion of procytokines to cytokines.

16. A method of alleviating inflammatory symptoms of a disease in a mammalian subject suffering from an inflammatory non-autoimmune disease, wherein the disease is a brain tumor, or a central nervous system viral infection or a central nervous system bacterial infection, which comprises administering glatiramer acetate to the subject in an amount and for a duration of time effective to inhibit matrix metalloproteinase so as to alleviate the inflammatory symptoms of the disease in the subject.

17. The method of claim 16, wherein the glatiramer acetate administration decreases the conversion of procytokines to cytokines.

18. The method of claim 16, wherein the amount of glatiramer acetate administered ranges from about 0.05 mg/kg of body weight to about 50 mg/kg of body weight.

* * * * *